(12) United States Patent
Schnabel et al.

(10) Patent No.: US 9,814,233 B2
(45) Date of Patent: *Nov. 14, 2017

(54) COMPOSITION COMPRISING A PESTICIDE, A SURFACTANT AND AN ALKOXYLATE OF 2-PROPYHEPTYLAMINE

(75) Inventors: Gerhard Schnabel, Elsenfeld (DE); Paul Klingelhoefer, Mannheim (DE); Marc Nolte, Mannheim (DE); Richard Roger Evans, Limburgerhof (DE); Gerd Kraemer, Kerzenheim (DE); Silke Zeyer, Gruenstadt (DE); Matthias Pfenning, Schwegenheim (DE)

(73) Assignee: BASF SE, Ludwigshafen (DE)

( * ) Notice: Subject to any disclaimer, the term of this patent is extended or adjusted under 35 U.S.C. 154(b) by 339 days.

This patent is subject to a terminal disclaimer.

(21) Appl. No.: 14/001,611

(22) PCT Filed: Feb. 27, 2012

(86) PCT No.: PCT/EP2012/053230
§ 371 (c)(1),
(2), (4) Date: Aug. 26, 2013

(87) PCT Pub. No.: WO2012/116939
PCT Pub. Date: Sep. 7, 2012

(65) Prior Publication Data
US 2013/0331262 A1    Dec. 12, 2013

Related U.S. Application Data

(60) Provisional application No. 61/447,156, filed on Feb. 28, 2011.

(30) Foreign Application Priority Data

Apr. 12, 2011 (EP) ..................... 11162051

(51) Int. Cl.
*A01N 33/08* (2006.01)
*A01N 25/30* (2006.01)
*C07C 217/08* (2006.01)

(52) U.S. Cl.
CPC ............. *A01N 33/08* (2013.01); *A01N 25/30* (2013.01); *C07C 217/08* (2013.01)

(58) Field of Classification Search
CPC ........ A01N 25/30; A01N 57/20; A01N 33/08; C07C 217/08
USPC .......................................... 504/100; 514/668
See application file for complete search history.

(56) References Cited

U.S. PATENT DOCUMENTS

| 4,460,789 A | 7/1984 | Casciani |
| 5,530,127 A | 6/1996 | Reif et al. |
| 5,668,085 A | 9/1997 | Forbes et al. |
| 5,750,468 A | 5/1998 | Wright et al. |
| 6,835,695 B2 | 12/2004 | Krause et al. |
| 8,492,326 B2 | 7/2013 | Klingelhoefer et al. |
| 8,618,179 B2 | 12/2013 | Klingelhoefer et al. |
| 2002/0016264 A1* | 2/2002 | Shannon et al. ............... 504/364 |
| 2002/0137634 A1 | 9/2002 | Krause et al. |
| 2006/0019828 A1 | 1/2006 | Becher et al. |
| 2007/0049498 A1 | 3/2007 | Brigance et al. |
| 2007/0249560 A1 | 10/2007 | Leatherman et al. |
| 2008/0261814 A1 | 10/2008 | Zhu et al. |
| 2009/0114879 A1 | 5/2009 | Hellsten et al. |
| 2009/0286684 A1 | 11/2009 | Scherl et al. |
| 2010/0160162 A1* | 6/2010 | Becher et al. ................. 504/206 |
| 2010/0317521 A1* | 12/2010 | Correia ................. A01N 57/20 504/206 |
| 2011/0039703 A1 | 2/2011 | Correia |
| 2011/0111961 A1* | 5/2011 | Sun ........................ A01N 25/30 504/323 |

(Continued)

FOREIGN PATENT DOCUMENTS

| CA | 2 785 239 | 7/2011 |
| DE | 102005037971 | 2/2007 |

(Continued)

OTHER PUBLICATIONS

Office Action, issued in co-assigned U.S. Appl. No. 13/048,946, dated Oct. 20, 2014.
Office Action, issued in co-assigned U.S. Appl. No. 13/048,946, dated Jan. 30, 2013.
Final Office Action, issued in co-assigned U.S. Appl. No. 13/048,946, dated Sep. 11, 2013.
Final Office Action dated in U.S. Appl. No. 13/048,946.
International Preliminary Report on Patentability, issued in PCT/EP2012/053230, dated May 3, 2013.

(Continued)

*Primary Examiner* — Johann R Richter
*Assistant Examiner* — Courtney Brown
(74) *Attorney, Agent, or Firm* — Brinks Gilson & Lione

(57) ABSTRACT

The present invention relates to a composition comprising a pesticide, a surfactant and an alkoxylate. Moreover, the invention relates to a concentrate comprising the surfactant and the alkoxylate; and to a process for preparing the composition by bringing into contact the concentrate and a pesticide; or by bringing into contact the pesticide, the surfactant and the alkoxylate; and to the use of the surfactant by addition to a mixture comprising the pesticide and the alkoxylate. The invention furthermore relates to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesirable plants and/or the crop plants and/or their environment. Furthermore, the invention relates to seed comprising the composition.

21 Claims, No Drawings

(56) References Cited

U.S. PATENT DOCUMENTS

| | | | |
|---|---|---|---|
| 2011/0177945 A1* | 7/2011 | Klingelhoefer | A01N 25/30 504/100 |
| 2011/0201497 A1 | 8/2011 | Klingelhoefer et al. | |
| 2011/0230342 A1 | 9/2011 | Klingelhoefer et al. | |
| 2014/0080701 A1 | 3/2014 | Klingelhoefer et al. | |
| 2014/0243201 A1 | 8/2014 | Klingelhoefer et al. | |

FOREIGN PATENT DOCUMENTS

| | | |
|---|---|---|
| EP | 0696572 | 2/1996 |
| HU | 45468 | 7/1988 |
| WO | WO 0197614 | 12/2001 |
| WO | WO 02102153 | 12/2002 |
| WO | WO02102153 A2 * | 12/2002 |
| WO | WO 2006034459 | 3/2006 |
| WO | WO 2007030312 | 3/2007 |
| WO | WO 2008111928 | 9/2008 |
| WO | WO 2009004044 | 1/2009 |
| WO | WO 2009120621 | 10/2009 |
| WO | WO2009120621 A2 * | 10/2009 |
| WO | WO 2010068746 | 6/2010 |
| WO | WO 2010068746 A2 * | 6/2010 |
| WO | WO 2011086115 | 7/2011 |
| WO | WO2011/113786 | 9/2011 |
| WO | WO 2011104211 | 9/2011 |
| WO | WO 2013/189777 | 12/2013 |

OTHER PUBLICATIONS

International Search Report, issued in PCT/EP2012/053230, dated Mar. 27, 2012.

Tsui, Martin T.K., et al. "Aquatic toxicity of glyphosate-based formulations: comparison between difference organisms and the effects of environmental factors", Chemosphere, vol. 52, (2003), pp. 1189-1197.

Office Action dated Jan. 13, 2015 in U.S. Appl. No. 14/281,304.

Office Action dated Jan. 12, 2015 in U.S. Appl. No. 14/089,045.

Office Action dated May 9, 2016 from U.S. Appl. No. 14/407,743, filed Dec. 12, 2014.

Gutman, Ivan, "The chemical formula $Cr_nH_{2n+2}$ and its mathematical background", The Teaching of Mathematics, 2008, p. 53-61, vol. XI, No. 2.

\* cited by examiner

COMPOSITION COMPRISING A PESTICIDE, A SURFACTANT AND AN ALKOXYLATE OF 2-PROPYHEPTYLAMINE

This application is a National Stage application of International Application No. PCT/EP2012/053230, filed Feb. 27, 2012, which claims the benefit of U.S. Provisional Application No. 61/447,156, filed Feb. 28, 2011, the entire contents of which are hereby incorporated herein by reference. This application also claims priority under 35 U.S.C. §119 to European Patent Application No. 11162051.4, filed Apr. 12, 2011, the entire contents of which is hereby incorporated herein by reference.

The present invention relates to a composition comprising a pesticide, a surfactant and an alkoxylate. Moreover, the invention relates to a concentrate comprising the surfactant and the alkoxylate; and to a process for preparing the composition by bringing into contact the concentrate and a pesticide; or by bringing into contact the pesticide, the surfactant and the alkoxylate; and to a use of the surfactant for adding to a mixture comprising the pesticide and the alkoxylate. The invention furthermore relates to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesirable plants and/or the crop plants and/or their environment. Furthermore, the invention relates to seed comprising the composition. The present invention comprises combinations of preferred features with other preferred features.

Agrochemical formulations comprising amine alkoxylates are generally known:

WO 2009/004044 discloses a herbicidal composition comprising a phenoxy-acid herbicide and an alkoxylated alkylamine as adjuvant, it being possible for the alkylamine, for example, to be a 2-propylheptylmethylamine which is alkoxylated with 3 to 20 ethylene oxide groups.

U.S. Pat. No. 5,668,085 discloses a herbicidal composition comprising an aqueous solution of glyphosate and surfactant. The surfactant may be an alkoxylated alkylamine, the alkyl group comprising 8 to 22 carbon atoms.

WO 2011/086115 discloses 2-propylheptylamine alkoxylates, their preparation, and agrochemical formulations comprising pesticide and the 2-propylheptylamine alkoxylates.

US20100317521 and US20110039703 disclose a formulation comprising glyphosate and, by way of surfactant, an alkoxylate of a branched alkyl amine.

Alkoxylated alkylamines, in particular commercially available ethoxylated tallow fatty amines (POEA), have important toxic properties (such as irritation of the skin and the eyes) and ecotoxic properties (such as high ecotoxicity to aquatic organisms such as algae and daphnias). Thus, for example, POEA (CAS No. 61791-26-2), which is frequently present in Roundup® herbicides as a wetter, is considered to be relatively toxic to aquatic organisms (Tsui and Chu, Chemosphere 2003, 52, 1189-1197).

It was therefore an object of the present invention to find an adjuvant which is well suited to pesticides, in particular herbicides such as glyphosate while being less toxic (especially lower toxicity to aquatic organisms). Furthermore, the adjuvant should make possible a storage-stable formulation of the pesticides. Another object was to increase the biological activity of the agrochemical composition. Finally, this adjuvant was to avoid phytotoxic side-effects.

The object was solved by a composition comprising a pesticide, a surfactant and an alkoxylate, wherein the alkoxylate is an amine alkoxylate (A)

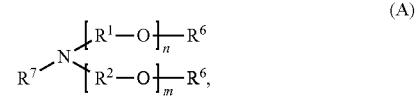

or a quaternized derivative (AQ)

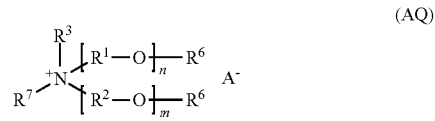

of the amine alkoxylate (A), where $R^1$, $R^2$, and $R^5$ independently of one another are ethylene, propylene, butylene or a mixture of these, $R^3$ is an H, —OH, —OR$^4$, —[R$^5$—O]$_p$—R$^6$, $C_1$-$C_6$-alkyl or an oxygen anion, $R^4$ is a $C_1$-$C_6$-alkyl, $C_2$-$C_6$-alkenyl or $C_2$-$C_6$-alkynyl, $R^6$ is an H, $C_1$-$C_6$-alkyl, $C_2$-$C_6$-alkenyl, $C_2$-$C_6$-alkynyl, —SO$_3$R$^a$, —P(O)OR$^b$OR$^c$, —CH$_2$CO$_2$R$^d$, or —C(O)R$^e$, $R^7$ is a $C_6$-$C_{14}$-alkyl, $R^a$ and $R^d$ independently of one another are an H, inorganic or organic cations, $R^b$ and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_2$-$C_{22}$-alkenyl, $C_2$-$C_{22}$-alkynyl, $C_6$-$C_{22}$-aryl or $C_7$-$C_{22}$-alkylaryl, n, m and p independently of one another have a value of from 1 to 30, A$^-$ is an agriculturally acceptable anion, or, if $R^3$ is an oxygen anion, A$^-$ is absent.

Preferably, the composition according to the invention comprises a pesticide and an alkoxylate, wherein the alkoxylate is an amine alkoxylate (A).

Preferably, n has a value of from 1 to 20, especially preferably from 1 to 15. Preferably, m has a value of from 1 to 20, especially preferably from 1 to 15. Preferably, p has a value of from 1 to 30, especially preferably from 1 to 20. The values of n, m and o are normally average values as they mostly arise upon the alkoxylation with alkoxides. Therefore, n, m and o can not only be integers, but also all values between the integers.

Preferably, in the case of the amine alkoxylate (A), the total of n and m is 2 to 40 and in its quaternized derivative (AQ) the total of n, m and p is 3 to 80. In the case of the amine alkoxylate (A) the total of n and m is especially preferably 3 to 30, specifically preferably 5 to 18, and specifically 8 to 14.

In a further especially preferred embodiment, the total of n and m is 6 to 9, in particular 6.5 to 8.5 and in particular 6.9 to 7.9. In a further especially preferred embodiment, the total of n and m is 11 to 40, in particular 12 to 30 and in particular 13.5 to 25. In a further especially preferred embodiment, the sum of n and m is 8 to 13, in particular 9 to 11.

In the case of the quaternized derivative (AQ) of the amine alkoxylate (A), the total of n, m and p is especially preferably 3 to 40 and specifically 5 to 25. In one especially preferred embodiment, the sum of n and m is 8 to 13, in particular 9 to 11.

$R^1$, $R^2$ and $R^5$ are preferably independently of one another ethylene, ethylene and propylene, ethylene and butylene, or ethylene, propylene and butylene. In a further preferred embodiment, $R^1$, $R^2$ and $R^5$ are propylene. In a further preferred embodiment, $R^1$, $R^2$ and $R^5$ are butylene. Especially preferably $R^1$, $R^2$ and $R^5$ independently of one another are ethylene, or ethylene and propylene. Very especially preferably, $R^1$, $R^2$ and $R^5$ are ethylene.

If $R^1$, $R^2$ or $R^5$ comprise a butylene radical, the latter may be present as a n-butylene, an isobutylene or a 2,3-butylene group, with n-butylene and isobutylene being preferred and n-butylene being most preferred.

$R^1$, $R^2$ and $R^5$ independently of one another may be a mixture of ethylene, propylene or butylene. In this context, for example one or all radicals $R^1$, $R^2$ and $R^5$ may comprise a mixture of these groups in each alkoxylate chain. Such mixtures can be linked to one another in any desired order, for example randomly or blockwise (such as one block ethylene and one block propylene). Also, it is possible for in each case one or more of the radicals $R^1$, $R^2$, and $R^5$ to form a complete alkoxylate chain composed of different alkylene groups. For example, $R^1$ and $R^2$ may be composed of ethylene and $R^5$ of propylene.

$R^3$ is preferably an H, —OH, $C_1$-$C_4$-alkyl or an oxygen anion, it is especially preferably an H, methyl, butyl or an oxygen anion. In a specifically preferred embodiment, $R^3$ is a methyl. In a further specifically preferred embodiment, $R^3$ is an oxygen anion. In a further specifically preferred embodiment, $R^3$ is an H.

$R^4$ is preferably a $C_1$-$C_6$-alkyl, in particular a methyl or butyl, especially butyl.

$R^6$ is preferably an H or $C_1$-$C_6$-alkyl, more preferably an H or methyl, especially H.

$R^7$ can be a linear or branched, saturated or unsaturated $C_6$-$C_{14}$-alkyl radical, such as hexyl, heptyl, octyl, nonyl, decyl, undecyl, dodecyl, tridecyl or tetradecyl. $R^7$ is preferably a branched, saturated alkyl radical. $R^7$ is preferably a $C_8$-$C_{13}$-alkyl radical. $R^7$ is especially preferably a branched alkyl radical $C_9H_{19}$, a branched $C_{13}H_{27}$-alkyl radical, 2-propylheptyl or 2-ethylhexyl. In a further especially preferred form, $R^7$ is especially preferably a branched alkyl radical $C_9H_{19}$, 2-propylheptyl or 2-ethylhexyl. In particular, $R^7$ is 2-propylheptyl. In one embodiment, $R^7$ is one of the above-mentioned radicals, with the exception In a preferred embodiment, $R^7$ is 2-ethylhexyl.

In a further preferred embodiment, $R^7$ is a branched alkyl radical $C_9H_{19}$. Examples are, inter alia, 2-methyl-1-octanol, 2-ethyl-1-heptanol, 2-propyl-1-hexanol, 3-methyl-4-hydroxymethyl-heptane, 3-methyl-3-hydroxymethyl-heptane or 2-hydroxymethyl-3-methyl-heptane. Preferably, the branched alkyl radical $C_9H_{19}$ comprises several different, branched alkyl radicals $C_9H_{19}$. The mean degree of branching is in this case 1.01 to 2.5, preferably 1.05 to 1.8, especially preferably 1.1 to 1.5, very especially preferably 1.2 to 1.3. The term "degree of branching" is here defined as known in principle, as the number of methyl groups in one alcohol molecule minus 1. The mean degree of branching is the statistic mean of the degrees of branching of all molecules of a sample. The preparation of these compounds is known, for example from U.S. 61/314,600.

In a further preferred embodiment, $R^7$ is a branched alkyl radical $C_{13}H_{27}$. An example is an isotridecyl radical.

In an especially preferred embodiment, $R^7$ is 2-propylheptyl. In this case, the alkoxylate corresponds to the amine alkoxylate (A1)

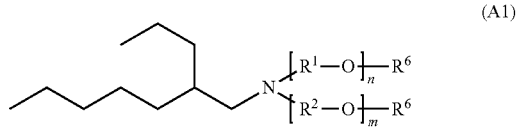

or the quaternized derivative (AQ1)

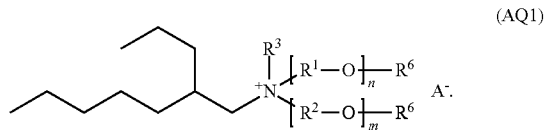

$R^a$ and $R^d$ are independently of one another H, or inorganic or organic cations, which may be singly or multiply positively charged. Examples of inorganic cations are cations of ammonium, Na$^+$, K$^+$, Mg$^{2+}$, Ca$^{2+}$, or Zn$^{2+}$. Examples of organic cations are methyl-ammonium, dimethylammonium, trimethylammonium, tetramethylammonium, (2-hydroxyethyl)ammonium, bis(2-hydroxyethyl)ammonium, tris (2-hydroxyethyl)-ammonium, tetra(2-hydroxyethyl) ammonium. Preferably, $R^a$ and $R^d$ independently of one another are H or inorganic cations. If an inorganic or organic cation is present, then the associated anionic group would be formed by the corresponding functional group (e.g., —SO$_3^-$, —P(O)O$^-$O$^-$, or —CH$_2$CO$_2^-$) on $R^6$.

$R^b$ and $R^c$ are preferably, independently of one another, H, inorganic or organic cations. Suitable inorganic or organic cations are those specified under $R^a$.

In another embodiment, in the quaternary derivative (AQ), the radicals $R^a$, $R^b$, $R^c$ and $R^d$ independently of one another may be organic cations, with the cationic group being the quaternary nitrogen cation of AQ itself. It would also be possible, therefore, for AQ to form a zwitterion, with the anionic group being formed by the corresponding functional group (e.g., —SO$_3^-$, —P(O)O$^-$O$^-$, or —CH$_2$CO$_2^-$) on $R^6$ in AQ, and the cationic group by the quaternary nitrogen of AQ. In this zwitterionic form of AQ, the presence of an agriculturally acceptable anion A$^-$ is optional.

$R^e$ is preferably $C_1$-$C_{12}$-alkyl, $C_6$-$C_{12}$-aryl, or $C_7$-$C_{12}$-alkylaryl, more preferably $C_1$-$C_6$-alkyl.

A$^-$ is an agriculturally acceptable anion, as they are generally known to the skilled worker. Preferably, A$^-$ is a halide (such as chloride or bromide), phosphate, sulfate or an anionic pesticide. Especially preferably, A$^-$ is an anionic pesticide, such as a glyphosate anion or glufosinate anion. If $R^3$ is an oxygen anion, an amine oxide is present. In this case, a further anion such as A$^-$ is absent.

In a preferred embodiment $R^1$ and $R^2$ independently of one another are ethylene, ethylene and propylene, ethylene and butylene, or ethylene, propylene and butylene, and the total of n and m is 2 to 60, preferably 2 to 40, especially preferably 3 to 30 and in particular 5 to 25. In a very particularly preferred embodiment, $R^1$ and $R^2$ are ethylene, ethylene and propylene, ethylene and butylene, or ethylene, propylene and butylene and the total of n and m is 5 to 18, more particularly 8 to 12, and especially 9 to 11.

In a further preferred embodiment, $R^1$ and $R^2$ independently of one another are both ethylene and propylene, and the total of n and m is 2 to 60, preferably 3 to 30, especially preferably 5 to 20 and in particular 8 to 14. Preferably the alkoxylate comprises 1.5 to 8 mol (preferably 2 to 6 mol) of propylene oxide and 5 to 20 mol (preferably 7 to 13 mol) of ethylene oxide.

In a particularly preferred embodiment $R^1$ and $R^2$ are ethylene, and the total of n and m is 2 to 60, preferably 2 to 40, especially preferably 3 to 30, specifically preferably 5 to 18 and in particular 8 to 14.

The compounds (A) and (AQ) may be present as mixtures of stereoisomers or as isolated stereoisomers. Tautomers and betaines are likewise encompassed by the structures (A) and (AQ).

In most cases, the composition according to the invention comprises from 0.1 to 90% by weight of the alkoxylate, preferably from 1 to 50% by weight and in particular from 3 to 30% by weight.

The term pesticide refers to at least one active substance selected from the group of the fungicides, insecticides, nematicides, herbicides, safeners, molluscicides, rodenticides and/or growth regulators. Preferred pesticides are fungicides, insecticides, herbicides and growth regulators. Especially preferred pesticides are herbicides and growth regulators. Mixtures of pesticides from two or more of the abovementioned classes may also be used. The skilled worker is familiar with such pesticides, which can be found, for example, in Pesticide Manual, 15th Ed. (2009), The British Crop Protection Council, London. The pesticides may also comprise salts, esters, optical isomers or tautomers. Suitable pesticides are (groups A) to M) are fungicides):

A) Respiration Inhibitors
   complex-III-inhibitors at the $Q_o$-site (for example strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, methyl 2-[2-(2,5-dimethylphenyloxymethyl)phenyl]-3-methoxyacrylate, 2-(2-(3-(2,6-dichlorophenyl)-1-methylallylideneamino-oxymethyl)phenyl)-2-methoxyimino-N-methylacetamide, pyribencarb, triclopyricarb/chlorodincarb, famoxadon, fenamidon;
   Complex-III-inhibitors of the $Q_i$-site: cyazofamid, amisulbrom;
   Complex-II-inhibitors (for example carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide and N-(2-(1,3,3-trimethylbutyl)phenyl)-1,3-dimethyl-5-fluoro-1H-pyrazole-4-carboxamide;
   other respiration inhibitors (for example complex I, uncouplers): diflumetorim; nitrophenyl derivatives: binapacryl, dinobuton, dinocap, fluazinam; ferimzone; organometal compounds: fentin salts such as fentin acetate, fentin chloride or fentine hydroxide; ametoctradin; and silthiofam;

B) Sterol Biosynthesis Inhibitors (SBI Fungicides)
   C14-Demethylase inhibitors (DMI fungicides):
   triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizole; pyrimidines, pyridines and piperazines: fenarimol, Nuarimol, pyrifenox, triforine;
   delta14-reductase inhibitors: aldimorph, dodemorph, dodemorph acetate, fenpropimorph, tridemorph, fenpropidin, piperalin, spiroxamine; 3-ketoreductase inhibitors: fenhexamid;

C) Nucleic Acid Synthesis Inhibitors
   phenylamides or acylamino acid fungicides: benalaxyl, benalaxyl-m, kiralaxyl, metalaxyl, metalaxyl-m (mefenoxam), ofurace, oxadixyl;
   others: hymexazole, octhilinone, oxolinic acid, bupirimate;

D) Cell Division and Cytoskeleton Inhibitiors
   tubulin inhibitors such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine;
   further cell division inhibitors: diethofencarb, ethaboxam, pencycuron, fluopicolid, zoxamid, metrafenon, pyriofenon;

E) Amino Acid Synthesis and Protein Synthesis Inhibitors
   methionine synthesis inhibitors (anilinopyrimidine): cyprodinil, mepanipyrim, pyrimethanil;
   protein synthesis inhibitors: blasticidin-S, kasugamycin, kasugamycin hydrochloride hydrate, mildiomycin, streptomycin, oxytetracyclin, polyoxin, validamycin A;

F) Signal Transduction Inhibitors
   MAP/histidine kinase inhibitors: fluoroimide, iprodione, procymidone, vinclozolin, fenpiclonil, fludioxonil;
   G-protein inhibitors: quinoxyfen;

G) Lipid and Membrane Synthesis Inhibitors
   Phospholipid biosynthesis inhibitors: edifenphos, iprobenfos, pyrazophos, isoprothiolane;
   Lipid peroxidation: dicloran, quintozene, tecnazene, tolclofos-methyl, biphenyl, chloroneb, etridiazole;
   Phospholipid biosynthesis and cell wall attachment: dimethomorph, flumorph, mandipropamid, pyrimorph, benthiavalicarb, iprovalicarb, valifenalate and 4-fluorophenyl N-(1-(1-(4-cyanophenyl)ethanesulfonyl)but-2-yl)carbamate;
   Compounds which affect cell membrane permeability and fatty acids: propamocarb, propamocarbhydrochloride H) "Multi-Site" Inhibitors
   inorganic active substances: Bordeaux mixture, copper acetate, copper hydroxide, copper oxychloride, basic copper sulfate, sulfur;
   Thio- and dithiocarbamates: ferbam, mancozeb, maneb, metam, metiram, propineb, thiram, zineb, ziram;
   organochlorine compounds (for example phthalimides, sulfamides, chloronitriles): anilazine, chlorothalonil, captafol, captan, folpet, dichlofluanid, dichlorophen, flusulfamide, hexachlorobenzene, pentachlorophenol and its salts, phthalid, tolylfluanid, N-(4-chloro-2-nitrophenyl)-N-ethyl-4-methylbenzenesulfonamide;
   guanidines and others: guanidine, dodine, dodine free base, guazatin, guazatin acetate, iminoctadin, iminoctadin triacetate, iminoctadin tris(albesilate), dithianon;

I) Cell Wall Biosynthesis Inhibitors
   glucan synthesis inhibitors: validamycin, polyoxin B;
   melanin synthesis inhibitors: pyroquilon, tricyclazole, carpropamid, dicyclomet, fenoxanil;

J) Resistance Inductors
   acibenzolar-5-methyl, probenazol, isotianil, tiadinil, prohexadione-calcium; phosphonates: fosetyl, fosetyl-aluminum, phosphorous acid and its salts;

K) Unknown Mode of Action
   bronopol, quinomethionate, cyflufenamid, cymoxanil, dazomet, debacarb, diclo-mezin, difenzoquat, difenzoquat-methyl sulfate, diphenylamine, fenpyrazamine, flumetover, flusulfamid, flutianil, methasulfocarb, nitrapyrin, nitrothal-isopropyl, oxine-copper, proquinazid, tebufloquin, tecloftalam, triazoxide, 2-butoxy-6-iodo-3-propylchromene-4-one, N-(cyclopropylmethoxyimino-(6-difluoromethoxy-2,3-difluorophenyl)methyl)-2-phenylacetamide, N'-(4-(4-chloro-3-trifluoromethyl-phenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanyl-propoxy)phenyl)-N-ethyl-N-methylformamidine, N-methyl-(1,2,3,4-tetrahydronaphthalen-1-yl)-2-{1-[2-(5-methyl-3-trifluoromethylpyrazol-1-yl)acetyl]piperidin-4-yl}thiazole-4-carboxylate, N-methyl-(R)-1,2,3,4-tetrahydronaphthalen-1-yl 2-{1-[2-(5-methyl-3-trifluoromethylpyrazol-1-yl)acetyl]piperidin-4-yl}thiazole-4-carboxylate, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 6-tert-butyl-8-fluoro-2,3-dimethylquinolin-4-yl methoxyacetate, N-methyl-2-{1-[(5-methyl-3-trifluoromethyl-1H-pyrazol-1-yl)acetyl]piperidin-4-yl}-N-[(1R)-1,2,3,4-tetrahydronaphthalen-1-yl]-4-thiazolecarboxamide, 3-[5-(4-methylphenyl)-2,3-dimethylisoxazolidin-3-yl]-pyridine, 3-[5-(4-chlorophenyl)-2,3-dimethylisoxazolidin-3-yl]-pyridine (pyrisoxazol), N-(6-methoxypyridin-3-yl)cyclopropanecarboxamide, 5-chloro-1-(4,6-dimethoxypyrimidin-2-yl)-2-methyl-1H-benzoimidazole, 2-(4-chlorophenyl)-N-[4-(3,4-dimethoxyphenyl)isoxazol-5-yl]-2-prop-2-ynyloxyacetamide;

L) Biological Fungicides, Plant Strengthening Agents
   *Ampelomyces quisqualis* (for example the product AQ 10® from Intrachem Bio GmbH & Co. KG, Germany), *Aspergillus flavus* (for example the product AFLA-GUARD® from Syngenta, Switzerland), *Aureobasidium pullulans* (for example the product BOTECTOR® from bio-ferm GmbH, Germany), *Bacillus pumilus* (for example strain NRRL No. B-30087 in SONATA® and BALLAD® Plus from AgraQuest Inc., USA), *Bacillus subtilis* (for example strain NRRL-No. B-21661 in RHAPSODY®, SERENADE®MAX and SERENADE® ASO from AgraQuest Inc., USA), *Bacillus subtilis* var. *amyloliquefaciens* FZB24 (for example the product TAEGRO® from Novozyme Biologicals, Inc., USA), *Candida oleophila* I-82 (for example the product ASPIRE® from Ecogen Inc., USA), *Candida saitoana* (for example the products BIOCURE® (in admixture with lysozym) and BIOCOAT® from Micro Flo Company, USA (BASF SE) and Arysta), chitosan (for example ARMOUR-ZEN from BotriZen Ltd., New Zealand), *Clonostachys rosea* f. *catenulata*, also known as *Gliocladium catenulatum* (for example J1446: PRESTOP® from Verdera, Finland), *Coniothyrium minitans* (for example the product CONTANS® from Prophyta, Germany), *Cryphonectria parasitica* (for example the product *Endothia parasitica* from CNICM, France), *Cryptococcus albidus* (for example the product YIELD PLUS® from Anchor Bio-Technologies, South Africa), *Fusarium oxysporum* (for example the products BIOFOX® from S.I.A.P.A., Italy, and FUSACLEAN® from Natural Plant Protection, France), *Metschnikowia fructicola* (for example the product SHEMER® from Agrogreen, Israel), *Microdochium dimerum* (for example the product ANTI BOT® from Agrauxine, France), *Phlebiopsis gigantea* (for example the product ROTSOP® from Verdera, Finland), *Pseudozyma flocculosa* (for example the product SPORODEX® from Plant Products Co. Ltd., Canada), *Pythium oligandrum* DV74 (for example the product POLYVERSUM® from Remeslo SSRO, Biopreparaty, Czech Republic), *Reynoutria sachlinensis* (for example the product REGALIA® from Marrone Biolnnovations, USA), *Talaromyces flavus* V117b (for example the product PROTUS® from Prophyta, Germany), *Trichoderma asperellum* SKT-1 (for example the product ECO-HOPE® from Kumiai Chemical Industry Co., Ltd., Japan), *T. atroviride* LC52 (for example the product SENTINEL® from Agrimm Technologies Ltd, New Zealand), *T. harzianum* T-22 (for example the product PLANTSHIELD® from Bio-Works Inc., USA), *T. harzianum* TH 35 (for example the product ROOT PRO® from Mycontrol Ltd., Israel), *T. harzianum* T-39 (for example the products TRICHODEX® and TRICHODERMA 2000® from Mycontrol Ltd., Israel and Makhteshim Ltd., Israel), *T. harzianum* and *T. viride* (for example the product TRICHOPEL from Agrimm Technologies Ltd, New Zealand), *T. harzianum* ICC012 and *T. viride* ICC080 (for example the product REMEDIER® WP from Isagro Ricerca, Italy), *T. polysporum* and *T. harzianum* (for example the product BINAB® from BINAB Bio-Innovation AB, Sweden), *T. stromaticum* (for example the product TRICOVAB® from C.E.P.L.A.C., Brazil), *T. virens* GL-21 (for example the product SOILGARD® from Certis LLC, USA), *T. viride* (for example the products TRIECO® from Ecosense Labs. (India) Pvt. Ltd., India and BIO-CURE® F from T. Stanes & Co. Ltd., India), *T. viride* TV1 (for example the product *T. viride* TV1 from Agribiotec srl, Italy), *Ulocladium oudemansii* HRU3 (for example the product BOTRY-ZEN® from Botry-Zen Ltd, New Zealand);

M) Growth Regulators
   abscisic acid, amidochlor, ancymidole, 6-benzylaminopurine, brassinolide, butralin, chlormequat (chlormequat chloride), choline chloride, cyclanilid, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidid, mepiquat (mepiquat chloride), metconazole, naphthaleneacetic acid, N-6-benzyladenine, paclobutrazole, prohexadione (prohexadione-calcium), prohydrojasmone, thidiazuron, triapenthenol, tributylphosphorotrithioate, 2,3,5-triiodo-benzoic acid, trinexapac-ethyl and uniconazole;

N) Herbicides
   acetamide: acetochlor, alachlor, butachlor, dimethachlor, dimethenamid, flufenacet, mefenacet, metolachlor, metazachlor, napropamid, napronanilid, pethoxamid, pretilachlor, propachlor, thenylchlor;
   amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperat, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxyacetic acid (2,4-D), 2,4-DB, dichlorprop, MCPA, MCPA-thioethyl, MCPB, mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxypyrimidin-2-yl)urea;

triazines: ametryne, atrazine, cyanazine, dimethametryne, ethiozine, hexazinone, metamitron, metribuzine, prometryne, simazine, terbuthylazine, terbutryne, triaziflam;

ureas: chlortoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, orthosulfamuron, penoxsulam, propoxycarbazone, pyribambenz-propyl, pyribenzoxim, pyriftalide, pyriminobac-methyl, pyrimisulfan, pyrithiobac, pyroxasulfon, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamid, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridon, flurtamon, indanofan, isoxaben, isoxaflutol, lenacil, propanil, propyzamide, quinclorac, quinmerac, mesotrione, methylarsenic acid, naptalam, oxadiargyl, oxadiazone, oxaziclomefon, pentoxazone, pinoxaden, pyraclonil, pyraflufen-ethyl, pyrasulfotol, pyrazoxyfen, pyrazolynate, quinoclamin, saflufenacil, sulcotrione, sulfentrazone, terbacil, tefuryltrione, tembotrione, thiencarbazone, topramezone, 4-hydroxy-3-[2-(2-methoxyethoxymethyl)-6-trifluoromethylpyridin-3-carbonyl]bicyclo[3.2.1]oct-3-en-2-one, ethyl(3-[2-chloro-4-fluoro-5-(3-methyl-2,6-dioxo-4-trifluoromethyl-3,6-dihydro-2H-pyrimidin-1-yl)phenoxy]pyridin-2-yloxy)acetate, methyl 6-amino-5-chloro-2-cyclo-propylpyrimidine-4-carboxylate, 6-chloro-3-(2-cyclopropyl-6-methylphenoxy)-pyridazin-4-ol, 4-amino-3-chloro-6-(4-chlorophenyl)-5-fluoropyridin-2-carboxylic acid, methyl 4-amino-3-chloro-6-(4-chloro-2-fluoro-3-methoxyphenyl)pyridin-2-carboxylate and methyl 4-amino-3-chloro-6-(4-chloro-3-dimethylamino-2-fluorophenyl)pyridin-2-carboxylate;

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoat, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, insect growth inhibitors: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonists: endosulfan, ethiprole, fipronil, vaniliprole, pyrafluprole, pyriprole, N-5-amino-1-(2,6-dichloro-4-methylphenyl)-4-sulfinamoyl-1H-pyrazole-3-thiocarbox-amide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacyprim, hydramethylnone;

decouplers: chlorfenapyr;

inhibitors of oxidative phosphorylation: cyhexatin, diafenthiuron, fenbutatin oxide, propargite;

insect ecdysis inhibitors: cryomazin;

'mixed function oxidase' inhibitors: piperonyl butoxide;

sodium channel blockers: indoxacarb, metaflumizon;

others: benclothiaz, bifenazate, cartap, flonicamid, pyridalyl, pymetrozin, sulfur, thiocyclam, flubendiamid, chlorantraniliprole, cyazypyr (HGW86); cyenopyrafen, flupyrazofos, cyflumetofen, amidoflumet, imicyafos, bistrifluoron and pyrifluquinazone.

Examples of safeners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (CAS 71526-07-3) and 2,2,5-trimethyl-3-(dichloroacetyl)-1,3-oxazolidine (CAS 52836-31-4).

Preferred pesticides comprise at least one pesticide with at least one H-acidic group (such as carboxylic acid group, phosphonic acid group, phosphinic acid group) or the anionic salts thereof (e.g., mono, di or tri salts). These anionic salts of the pesticides with an H-acidic group are also suitable as anionic pesticides in group A⁻. Preferred pesticides with an H-acidic group are herbicides with an H-acidic group. Examples of herbicides with an H-acidic group are amino acid analogs (such as glyphosate or glufosinate) or imidazolinones (such as imazamethabenz, imazamox, imazapic, imazapyr, imazaquin, imazethapyr).

Particularly preferred pesticides with an H-acidic group are glyphosate and glufosinate. In another preferred embodiment, pesticides with an H-acidic group are imidazolinones.

Especially preferably, the pesticide comprises a pesticide with an H-acidic group and one further pesticide. In another embodiment the pesticide comprises mixtures of at least two pesticides with an H-acidic group, and optionally further pesticides (such as at least one fungicide, herbicide, insecticide, and/or safener, with fungicides and/or herbicides being preferred).

In a further preferred embodiment, the pesticide comprises glyphosate (for example as the free acid, sodium salt, sesquisodium salt, potassium salt, dipotassium salt, ammonium salt, diammonium salt, dimethylammonium salt, trimesium salt or isopropylamine sale) or glufosinate (for example as the ammonium salt). With particular preference the pesticide comprises glyphosate (for example as the potassium salt, ammonium salt or isopropylamine salt). With particular preference the pesticide comprises glyphosate or glufosinate, and additionally a further herbicide. In another preferred embodiment the pesticide comprises glyphosate or glufosinate, and additionally a further pesticide (such as at least one fungicide, herbicide, insecticide and/or safener, with fungicides and/or herbicides being preferred).

Specifically preferably, the pesticide comprises glyphosate and at least one further herbicide selected from the following list:
acetochlor, acifluorofen, aclonifen, acrolein, alachlor, ametryn, amidosulfuron, amitrole, anilofos, asulam, atrazine, azafenidin, azimsulfuron, benazolin, benfluralin, benfuresate, bensulfuron-methyl, bensulide, bentazon, benzofenap, bialaphos, bifenox, bromacil, bromobutide, bromofenoxim, bromoxynil, butachlor, butamifos, butralin, butroxydim, butylate, cafenstrole, carbetamide, carfentrazone-ethyl, chlomethoxyfen, chloroamben, chlorobromuron, chloroidazon, chloroimuron-ethyl, chloronitrofen, chloroacetic acid, chlorotoluron, chloropropham, chlorosulfuron, chlorothal-dimethyl, chlorothiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-D,2,4-DB, daimuron, dalapon, desmedipham, desmetryn, dicamba, dichlobenil, dichloroprop, diclofop-methyl, difenzoquat, diflufenican, dimefuron, dimepiperate, dimethachlor, dimethametryn, dimethenamid, dinitramine, dinoterb, diphenamid, diquat, dithiopyr, diuron, endothall, EPTC, esprocarb, ethalfluralin, ethametsulfuron-methyl, ethofumesate, ethoxysulfuron, etobenzanid, fenac, fenoxaprop, fenoxaprop-ethyl, fenuron, flamprop, flampropmethyl, flazasulfuron, fluazifop-butyl, fluchloralin, flumetsulam, flumiclorac, flumiclorac-pentyl, flumioxazin, fluometuron, fluorochloridone, fluoroglycofen, fluoroglycofen-ethyl, flupoxam, flupropanate, flurenol, fluridone, fluoroxypyr-1-methylheptyl, flurtamone, fluthiacet-methyl, fomesafen, fosamine, glufosinate, halosulfuron, haloxyfop-methyl, hexazinone, imazameth, imazamethabenz, imazamox, imazapic, imazapyr, imazaquin, imazethapyr, imazosulfuron, indanofan, ioxynil, isoproturon, isouron, isoxaben, isoxaflutole, isoxapyrifop, lactofen, lenacil, linuron, MCPA, MCPB, mecoprop, mefenacet, mesotrione, metamitron, metazachlor, methabenzthiazuron, methylarsonic acid, methyldymron, metobenzuron, metobromuron, metolachlor, metosulam, metoxuron, metribuzin, metsulfuron, molinate, monolinuron, naproanilide, napropamide, naptalam, neburon, nicosulfuron, nonanoic acid, norflurazon, orbencarb, oryzalin, oxadiargyl, oxadiazon, oxasulfuron, oxyfluorfen, paraquat, pebulate, pendimethalin, pentanochlor, pentoxazone, phenmedipham, picloram, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfamic acid, sulfentrazone, sulfometuron, sulfosulfuron, TCA, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, 2,3,6-trichlorobenzoic acid, triclopyr, trietazine, trifluralin, triflusulfuron, vernolate.

In a further, specifically preferred embodiment, the pesticide comprises imazamox and at least one further herbicide selected from among the following classes b1) to b15): b1) lipid biosynthesis inhibitors: chloroazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylae, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate, bensulide and pinoxaden; b2) ALS inhibitors: amidosulfuron, azimsulfuron, bensulfuron, chloroimuron, chlorosulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan; b3) photosynthesis inhibitors: atraton, atrazine, ametryne, aziprotryne, cyanazine, cyanatryn, chloroazine, cyprazine, desmetryne, dimethametryne, dipropetryn, eglinazine, ipazine, mesoprazine, methometon, methoprotryne, procyazine, proglianzine, prometon, prometryne, propazine, sebuthylazne, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate and pyridafol; b4) protoporphyringogen-IX oxidase inhibitors: acifluorofen, bifenox, chlomethoxyfen, chloronitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen, etnipromid, saflufenacil and bencarbazone; b5) bleacher herbicides: metfluazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethyl-phenoxy)-2-(4-trifluoromethylphenyl)pyrimidine, disclosed in EP 723960, topramezone, 4-hydroxy-3-{[2-methyl-6-(trifluoromethyl)-3-pyridinyl]carbonyl}bicyclo[3.2.1]oct-3-en-2-one, disclosed in WO 00/15615, 4-hydroxy-3-{[2-(2-methoxyethoxy)methyl-6-(trifluoromethyl)-3-pyridinyl]carbonyl}bicyclo[3.2.1]oct-3-en-2-one, disclosed in WO 01/94339, 4-hydroxy-3-[4-(methylsulfonyl)-2-nitrobenzoyl]bicyclo[3.2.1]-oct-3-en-2-one, disclosed in EP 338992, 242-chloro-4-(methylsulfonyl)-3-[(2,2,2-trifluoroethoxy) methyl]-3-hydroxy-3-cyclohexen-1-one (disclosed in DE 19846792) and pyrasulfotole; b6) EPSP synthase inhibitors: glyphosate; b7) glutamine synthase inhibitors: glufosinate and bilanaphos; b8) DHP synthase inhibitors: asulam; b9) mitosis inhibitors: benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham; b10) VLCFA inhibitors: acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane; b11) cellulose biosynthesis inhibitors: dichlobenil, chlorthiamid, isoxaben and flupoxam; b12) decoupler herbicides: dinofenate, dinoprop, dinosam, dinoseb, dinoterb, DNOC, etinofen and medinoterb; b13) auxin herbicides: clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr, benazolin and aminopyralid; b14) auxin transport inhibitors: naptalam, diflufenzopyr; b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam, methyl bromide.

Suitable surfactants are, in particular anionic, cationic, nonionic and amphoteric surfactants, block polymers and polyelectrolytes. Preferred surfactants are anionic surfactants and nonionic surfactants. In an especially preferred embodiment, surfactants are anionic surfactants. In a further especially, surfactants are nonionic surfactants.

Suitable anionic surfactants are surfactants comprising an anionic group such as sulfonates, sulfates, phosphates or carboxylates. The anionic surfactants can be employed in the form of alkali metal, alkaline-earth metal or ammonium salts, or else in the form of the free acid. Preferred anionic surfactants are sulfonates and phosphates. In one embodiment, phosphonates are especially preferred. In a further embodiment, phosphates are especially preferred.

Examples of sulfonates are alkylarylsulfonates, diphenylsulfonates, alpha-olefinsulfonates, ligninosulfonates, sulfonates of fatty acids and of oils, sulfonates of ethoxylated alkylphenols, sulfonates of condensed naphthalenes, sulfonates of dodecyl- and tridecylbenzenes, sulfonates of naphthalenes and alkylnaphthalenes, sulfosuccinates or sulfosuccinamates. Preferred sulfonates are alkylarylsulfonates, especially preferred is $C_{8-18}$-alkylbenzenesulfonate. Such alkylarylsulfonates can be prepared by sulfonating alkylbenzene with sulfur trioxide. Alkylarylsulfonates are commercially available as $C_{10-13}$-alkylbenzenesulfonate, the free acid, or $C_{10-13}$-alkylbenzenesulfonate, alkanolamine salt. The alkylarylsulfonates are preferably present in the form of the free acid or as an alkanolamine salt (for example triethanolamine).

Examples of sulfates are sulfates of fats and oils, of ethoxylated alkylphenols, of $C_{6-32}$-alcohols, of ethoxylated alcohols, or of fatty acid esters. Preferred sulfates are sulfates of $C_{12-22}$-alcohols and of ethoxylated $C_{6-32}$-alcohols.

Examples of phosphates are phosphate esters. Preferred phosphates are phosphate esters of alkoxylates, such as phosphate esters of alkanol alkoxylates. Preferred phosphates are phosphate esters of $C_{6-22}$-alkanol alkoxylates (in particular $C_{8-14}$-alkanol alkoxylates). The alkoxylate units is usually composed of ethylene oxide and/or propylene oxide. In most cases, it has a mean number of alkoxide units in the range of from 6 to 30, preferably from 12 to 18. The phosphates are preferably in the form of the free acid or as alkanolamine salt (for example triethanolamine). The phosphate esters can be present as phosphate monoesters or phosphate diesters or as a mixture of these.

Examples of carboxylates are alkyl carboxylates and carboxylated alcohol ethoxylates or alkylphenol ethoxylates. Preferred carboxylates are alkyl carboxylates, such as those having 8-32 carbon atoms, in particular 10 to 22 carbon atoms. Examples are fatty acids, which may also be present in industrial mixtures of chain lengths of, for example, from 10 to 22 carbon atoms.

Suitable nonionic surfactants are alkoxylates, N-alkylated fatty acid amides, amine oxides, esters or sugar-based surfactants. Preferred nonionic surfactants are alkoxylates and sugar-based surfactants. In one embodiment, alkoxylates are especially preferred. In a further embodiment, sugar-based surfactants are especially preferred.

Examples of alkoxylates are compounds such as alcohols, alkylphenols, amines, amides, arylphenols, fatty acids or fatty acid esters which have been alkoxylated. Ethylene oxide and/or propylene oxide may be used for the alkoxylation, preferably ethylene oxide. Preferred alkoxylates are alkanol alkoxylates, preferably linear and branched, saturated or unsaturated $C_{4-22}$-alkanol alkoxylates, the alkoxylate being composed of ethylene oxide and/or propylene oxide. The alkanol alkoxylate typically comprises a mean number of alkoxide units in the range of from 2 to 50, preferably from 2.2 to 20, especially preferably from 2.8 to 12 and in particular from 2.8 to 8. Alkanol alkoxylates are commercially available from BASF SE as Emulan® types, Plurafac® types or Lutensol® types.

Examples of N-alkylated fatty acid amides are fatty acid glucamides or fatty acid alkanolamides.

Examples of esters are fatty acid esters, glycerol esters or monoglycerides.

Examples of sugar-based surfactants are sorbitans, ethoxylated sorbitans, sucrose esters and glucose esters or alkyl polyglucosides. Preferred sugar-based surfactants are $C_{6-18}$-alkyl polyglucosides, for example with a D.P. (degree of polymerization) of from 1.2 to 1.9.

Suitable cationic surfactants are quaternary surfactants, for example quaternary ammonium compounds with one or two hydrophobic groups, or salts of long-chain primary amines.

Suitable amphoteric surfactants are alkylbetains and imidazolines.

Suitable block polymers are block polymers of the A-B or the A-B-A type, it being possible for the blocks A and B to be polyethylene oxide, polypropylene oxide or polybutylene oxide. Preferred examples are A-B block polymers composed of polyethylene oxide and polypropylene oxide, or polyethylene oxide and polybutylene oxide; and A-B-A block polymers composed of polyethylene oxide and polypropylene oxide, or polyethylene oxide and polybutylene oxide (in particular polyethylene oxide/polypropylene oxide/polyethylene oxide). Others which are furthermore also suitable are block polymers of the A-B-C type comprising polyethylene oxide, polypropylene oxide and polybutylene oxide.

Suitable polyelectrolytes are polyacids or polybases. Examples of polyacids are alkali metal salts of polyacrylic acid. Examples of polybases are polyvinylamines or polyethyleneamines.

Especially preferred is at least one surfactant selected among sulfonates, phosphates, alkoxylates and sugar-based surfactants (e.g. in compositions comprising an alkoxylate, wherein $R^7$ is a branched alkyl radical $C_9H_{19}$, 2-propylheptyl or 2-ethylhexyl). Very especially preferred is at least one surfactant selected among alkylarylsulfonates, phosphate ester of alkoxylates, alkanol alkoxylates and alkyl polyglucosides (e.g. in compositions comprising an alkoxylate, wherein $R^7$ is a branched alkyl radical $C_9H_{19}$, 2-propylheptyl or 2-ethylhexyl).

A series of surfactants are advantageously suitable for the composition according to the invention:
a) In a preferred embodiment, the surfactant is a $C_{16-18}$-alkanol alkoxylate, where the alkoxylate is composed of ethylene oxide and/or propylene oxide and the alkanol alkoxylate has a mean number of alkoxide units in the range of from 12 to 35, preferably from 17 to 26.
b) In a further preferred embodiment, the surfactant is a $C_{10}$-Guerbet alkanol alkoxylate, where the alkoxylate is composed of ethylene oxide and the alkanol alkoxylate has a mean number of alkoxide units in the range of from 2 to 8, preferably from 2.5 to 6.
c) In a further preferred embodiment, the surfactant is an iso-$C_{13}$-alkanol alkoxylate, where the alkoxylate is composed of ethylene oxide and the alkanol alkoxylate has a mean number of alkoxide units in the range of from 3 to 10, preferably from 4.5 to 8.
d) In a further preferred embodiment, the surfactant is a $C_{4-8}$-alkanol alkoxylate, where the alkoxylate is composed of ethylene oxide and the alkanol alkoxylate has a mean number of alkoxide units in the range of from 2 to 9, preferably from 3.5 to 7.
e) In a preferred embodiment, the surfactant is a $C_{8-10}$-alkylpolyglucoside with a D.P. of from 1.4 to 1.9, preferably from 1.6 to 1.8.
f) In a further preferred embodiment, the surfactant is a $C_{8-14}$-alkylbenzenesulfonate.
g) In a further preferred embodiment, the surfactant is a phosphate ester of $C_{8-14}$-alkanol alkoxylates.

Among the aforementioned series the surfactants b), c), e) and f) are more advantageously suitable.

In another embodiment, the surfactant is selected from the groups b1) to b5):
b1) a nonionic surfactant of the formula $R^{11}X_n$ and polyalkoxylated derivatives thereof, wherein $R^{11}$ is selected from aliphatic or aromatic residues having at least eight carbon atoms; X is selected from hydroxy, —O—($C_1$-$C_6$-alkyl), —O—($C_3$-$C_6$-alkenyl), amine, amide, or ester; and n is 1, 2, 3, 4, 5 or 6;
b2) an anionic surfactant of the formula $R^{11}Y_n$, wherein $R^{11}$ is selected from aliphatic or aromatic residues having at least eight carbon atoms; Y is selected from carboxylate, sulfonate, sulfate, phosphate, or phosphonate; and n is 1, 2, 3, 4, 5 or 6;
b3) a cationic surfactant;
b4) a zwitterionic surfactant; or
b5) a polymeric surfactant.

In particular, the surfactant may be selected from b1) nonionic surfactants of the formula $R^{11}X_n$ and polyalkoxylated derivatives thereof (as defined below), wherein $R^{11}$ is selected from aliphatic or aromatic residues having at least eight carbon atoms; X is selected from hydroxy, —O—($C_1$-$C_6$-alkyl), —O—($C_3$-$C_6$-alkenyl), amine, amide, or ester; and n is 1, 2, 3, 4, 5, or 6. Glyceryl for example would be propyl ($R^{11}$) containing three hydroxy groups (X). In case X is hydroxy, preferably at least one of the hydroxy groups is polyalkoxylated. The surfactant b1 is preferably selected from polyalkoxylated derivatives of the formula $R^{11}X_n$. Preferred amides are mono- or di-$C_1$-$C_8$-alkylamides and mono- or di-$C_1$-$C_8$-acylamides, wherein the alkylamides are particularly preferred.

$R^{11}$ is preferably selected from aliphatic or aromatic residues having at least 10, more preferably at least 12 carbon atoms. The aromatic residues may contain aliphatic and/or aromatic substitutents. In another form, $R^{11}$ is selected from aliphatic or aromatic residues having from 8 to 30, preferably from 10 to 22 and in particular from 12 to 18 carbon atoms. $R^{11}$ is preferably selected from aliphatic residues having at least 10, more preferably at least 12 carbon atoms. The aliphatic residues may be linear or branched, saturated or unsaturated. Examples for $R^{11}$ are: 2,4,6-triisopropylphenyl, polystyrylphenyl, n-octyl, n-decyl, n-undecyl, n-dodecyl, n-tridecyl, n-tetradecyl, n-hexadecyl, n-octadecyl, 2-ethylhexyl, 1-methylnonyl, 2-propylheptyl, 1-methyldecyl, 1-methylundecyl, isotridecyl, n-tetradecenyl, 1-methylpentadecyl, n-hexadecenyl, n-hexadecadienyl, n-octadecenyl, n-octadecadienyl.

The surfactant b1 is preferably selected from nonionic surfactants of polyalkoxylated derivatives of the formula $R^{11}X_n$ wherein $R^{11}$ is selected from aliphatic or aromatic residues having at least eight carbon atoms; and X is selected from hydroxy, amine or amide. The polyalkoxylated derivatives of the formula $R^{11}X_n$ contain a polyalkoxylate residue, which may contain 5 to 50 (preferably 6 to 25 and in particular 6 to 20) equivalents of a $C_2$-$C_6$-alkylenoxide. Typically, $R^{11}X_n$ contains one or two polyalkoxylate residues per each residue X, depending on the free valences of X. In case X is hydroxy, said hydroxy group may contain one polyalkoxylate residue per each hydroxy group. In case X is amine, said amine group may contain one or two, preferably two, polyalkoxylate residues per each amine group. Preferably, the alkyleneoxide is selected from ethylene oxide, propylen oxide, butyleneoxide, and mixtures thereof. In a preferred form, the polyalkoxylated derivatives of the formula $R^{11}X_n$ contain polyethyleneoxide residues, which may contain 6 to 15 equivalents of an ethyleneoxide. Preferred are poly($C_2$-$C_6$ alkoxylate) residues, such as polyethyleneoxide, polypropyleneoxide. The alkyleneoxide units may be in random or block sequence (such as EO-PO-EO). The alkyleneoxide units may further substituted with other functional groups, such as alkyl, acyl, or polyethylene glycol groups. The polyalkoxylate residue may be terminated by hydrogen or any organic group, such as $C_1$-$C_8$ alkyl.

In a further embodiment, X may be selected from ethoxylated derivatives of amides, which may contain 1 to 20 equivalents of ethylene oxide.

In a further embodiment, X may be selected from alkoxylated derivatives of esters, wherein the polyalkoxylate residue contains 1 to 50 (preferably 2 to 25 and in particular 5 to 25) equivalents of an $C_2$-$C_4$-alkylenoxide.

Especially preferred surfactant b1) of the formula $R^{11}X_n$ are
- ethoxylated isotridecylalcohols containing 5, 6, 8, 15, or 20 ethylenoxide equivalents, and optionally terminated with a methyl group,
- alkoxylated 2-propylheptylalcohols containing 10 ethylenoxide equivalents, and optionally 2 or 5 propylene oxide equivalents,
- alkoxylated linear, saturated fatty alcohols, such as alkoxylated linear, saturated $C_{16-18}$ fatty alcohols containing 2 to 80 ethylenoxide equivalents,
- alkoxylated 2-propylheptylamines, e.g. containing 7 to 15 ethylenoxide equivalents,
- alkoxylated tallow amine, e.g. containing 10 to 20 ethylenoxide equivalents,
- alkoxylated isodecanol, e.g. containing 5 to 15 ethylenoxide equivalents,
- alkoxylated $C_{10}$-Guerbet alcohols, e.g. containing 5 to 15 ethylenoxide equivalents,
- alkoxylated $C_{13/15}$-oxoalcohols, e.g. containing 5 to 30 ethylenoxide equivalents,
- alkoxylated linear, saturated fatty alcohols, which contain at least one ethylenoxide equivalent and at least one $C_{3-6}$ alkyleneoxide equivalent,
- ethoxylated n-dodecanol (8 EO),
- ethoxylated fatty acid (saturated or unsaturated) containing 5 to 20 ethylenoxide equivalents, optionally terminated by a acyl (e.g. derived from a fatty acid),
- ethoxylated fatty acid monoamide (saturated or unsaturated) containing 5 to 20 ethylenoxide equivalents,
- ethoxylated fatty acid diamide (saturated or unsaturated) containing 10 to 40 ethylenoxide equivalents,
- ethoxylated glycerol containing a total of 10 to 45 ethylenoxide equivalents and up to 15 in each polyethoxylate chain, optionally terminated by $C_8$-$C_{22}$-alkyl.

The surfactant b2) may be selected from b2) anionic surfactants of the formula $R^{11}Y_n$, wherein $R^{11}$ is selected from aliphatic or aromatic residues having at least eight carbon atoms; Y is selected from carboxylate, sulfonate, sulfate, phosphate, or phosphonate; and Y is 1, 2, 3, 4, 5 or 6. The residue $R^{11}$ is defined as disclosed above for $R^{11}X_n$. The anionic surfactant may be present as alkali, alkaline earth, ammonium, or aliphatic amine (e.g. hydroxyethylammonium, trihydroxyethylammonium, tetrahydroxyethylammonium, trihydroxypropylammonium) salts.

Especially preferred surfactant b2) of the formula $R^{11}Y_n$ are
- aliphatic monocarboxylate, such as fatty acids or sarcosinates,
- aliphatic oligocarboxylates, such as malonate or succinate derivatives,
- sulfonamidocarboxylates,
- aliphatic or aromatic sulfates,
- polyethersulfates,
- amidopolyethersulfates,
- sulfated carboxylates, carbonic acid glycerides, or carbonic esters,
- aliphatic or aromatic sulfonates,
- sulfonated carboxylic esters or carboxylic amides,
- sulfosuccinic acid esters,
- polyethersulfonates,
- polyether phosphates, such as tristyryl polyetherphosphate or phosphate ester of polyalkoxylated fatty alcohol,
- polyether sulfate, such as fatty alcohol polyethersulfate,
- polyalkoxylated derivatives of the formula $R^{11}X_n$, wherein the polyalkoxylate residue is terminated by a residue Y.

The surfactant b3) may be selected from b3) cationic surfactants $R^{11}Z_n$, which usually comprise a lipophilic part, such as $R^{11}$ as disclosed above; a cationic group Z; wherein n is 1, 2, 3, 4, 5 or 6. Suitable cationic groups Z are ammonium; mono-, di-, tri-, or tetrasubstituted ammonium, wherein the substituents may be selected from $C_1$-$C_{10}$ alkyl (e.g. methyl, ethyl, propyl, allyl), benzyl, $C_1$-$C_8$-alkylether or a polyethylene glycol residue; di-$C_1$-$C_{12}$-alkylsulfonium; or nitrogen containing aromatic groups, such as N-substituted derivatives of pyrrol, pyridin, chinolin or isochinolin, imidazol, oxazol, thiazol. The cationic surfactant may be present as salt, e.g. salt of acetate, formiate, propionate, sulfonate, sulfate, methylsulfate, methylsulfonate, phosphate, or halogenide (e.g. chloride, bromide or iodide).

Especially preferred surfactant b3) selected from cationic surfactants are salts of
- trimethyl-$C_1$-$C_{20}$ alkylammonium
- $C_1$-$C_{20}$ alkylammonium,
- di-$C_1$-$C_{20}$ alkylammonium,
- tri-$C_1$-$C_{20}$ alkylammonium,
- benzyltri-$C_1$-$C_{20}$ alkylammonium,
- N-substituted pyridinium,
- derivatives of N,N'-$C_1$-$C_{12}$-dialkylimidazolium,
- derivatives of N—$C_1$-$C_{12}$-oxazolium,
- derivatives of N-$C_1$-$C_{12}$-thiazolium,
- $C_3$-$C_{20}$-alkyl-dimethylsulfonium,
- $C_1$-$C_{20}$ carboxylic acid esters of 2-hydroxyethyl-trimethylammonnium,
- $C_1$-$C_{20}$ carboxylic acid esters of ethoxylated (1-15 EO) 2-hydroxyethyl-trimethylammonnium,
- tri-$C_1$-$C_{20}$ alkyl-$C_1$-$C_{20}$ alkoxylammonium.

The surfactant b4) may be selected from b4) zwitterionic surfactants, which usually comprise a lipophilic part, such as $R^{11}$ as disclosed above, an anionic group, such as Y as disclosed above, and a cationic group Z as disclosed above.

Especially preferred surfactant b4) selected from zwitterionic surfactants are tri-$C_1$-$C_{20}$ alkylamin N-oxide,
betains, such as N,N,N-tri-$C_1$-$C_{20}$-alkylglycine,
aminocarboxylic acids,
dimethylammonium terminated ethoxylated $C_1$-$C_{20}$-alkylphosphonate,
derivatives of α-sulfated $C_3$-$C_{20}$-carbonic acid 2-(trimethylammonium)-ethylester,
ω-(tri-$C_1$-$C_{20}$-alkylammonium)-$C_2$-$C_{20}$-alkylsulfonic acid,
[(3-Dodecanoylamino-propyl)-dimethyl-ammonium]-acetic acid.

The surfactant b5) may be selected from b5) polymeric surfactants, which usually have a molecular weight of at least 2000 g/mol, preferably at least 5000 g/mol. The polymeric surfactant may be built from monomers, such as derivatives of N-vinyl amines, $C_2$-$C_4$ alkylen oxide, (meth)acrylates, (meth)acrylic acid, N-vinylformamides, N-vinylpyridines, AMPS. The monomers may be in random or block sequence. Suitable block polymers are block polymers of the A-B or A-B-A type comprising blocks of polyethylene oxide and polypropylene oxide, or of the A-B-C type comprising alkanol, polyethylene oxide and polypropylene oxide. The block polymers may be terminated by hydrogen or $C_1$-$C_4$ alkyl groups.

Most preferred surfactants from the groups b1) to b5) are selected from:
  polyether phosphates, in particular phosphate ester of polyalkoxylated fatty alcohol;
  alkoxylated 2-propylheptylamines, particular ethoxylated 2-propylheptylamines containing 7 to 15 ethylenoxide equivalents,
  alkoxylated tallow amine, in particular ethoxylated tallow amine containing 10 to 20 ethylenoxide equivalents,
  polyether sulfate, in particular lauryl alcohol polyethersulfate,
  ethoxylated isotridecylalcohols, in particular those containing at least 5 ethylenoxide equivalents,
  alkoxylated linear, saturated fatty alcohols, in particular alkoxylated linear, saturated $C_{16-18}$ fatty alcohols containing 10 to 80 ethylenoxide equivalents,
  alkoxylated isodecanols, in particular those containing 4 to 15 ethylenoxide equivalents,
  alkoxylated $C_{10}$-Guerbet alcohols, in particular those containing 5 to 15 ethylenoxide equivalents,
  alkoxylated $C_{13/15}$-oxoalcohols, in particular those containing 5 to 30 ethylenoxide equivalents,
  A-B-A type block polymers comprising blocks A of polyethylene oxide and blocks B of polypropylene oxide, which may have a molecular weight of from 800 to 8000 Da,
  alkoxylated linear, saturated fatty alcohols, which contain at least one ethylenoxide equivalent and at least one $C_{3-6}$ alkyleneoxide equivalent.

Specific, non-limiting examples for preferred surfactants from the groups b1) to b5) are the following surfactants:
T1 ethoxylated isotridecylalcohol containing 8 ethylenoxide equivalents.
T2 ethoxylated tallow amine containing 15 ethylenoxide equivalents.
T3 ethoxylated 2-propylheptylamines containing 10 ethylenoxide equivalents.
T4 phosphate ester of polyalkoxylated fatty alcohol, commercially available as Klearfac® AA-270 from BASF SE.
T5 alkoxylated linear, saturated $C_{16-18}$ fatty alcohols containing 2 to 20 ethylenoxide equivalents and 2 to 20 propyleneoxide equivalents.
T6 lauryl alcohol polyethersulfate containing 10 ethylenoxide equivalents, sodium salt.
T7 ethoxylated isotridecylalcohol containing 5 ethylenoxide equivalents.
T8 ethoxylated isotridecylalcohol containing 4 ethylenoxide equivalents.
T9 ethoxylated isotridecylalcohol containing 3 ethylenoxide equivalents.
T10 ethoxylated pentanol containing 4 ethylenoxide equivalents.
T11 Polyoxyethylen(20)-sorbitan-monolaurat.

The composition may comprise at least one surfactant, for example one, two or three surfactants.

In one embodiment, the composition comprises at least two different surfactants. Preferably, the composition comprises one nonionic and one anionic surfactant, two different anionic surfactants, or two different nonionic surfactants.

Suitable examples for two nonionic surfactants are two alkoxylates, preferably two different alkanol alkoxylates.

Suitable examples of two anionic surfactants are one sulfonate and one phosphate, preferably one alkylarylsulfonate and one phosphate ester of alkoxylates, in particular one $C_{8-18}$-alkylbenzylsulfonate and one phosphate ester of alkanol alkoxylates.

Suitable examples of one nonionic and one anionic surfactant are, in a first embodiment, one alkoxylate and one sulfonate, preferably one alkanol alkoxylate and one alkylarylsulfonate; in a second embodiment one alkylpolyglucoside and one sulfonate, preferably one $C_{6-18}$-alkylpolyglucoside with a D.P. of from 1.2 to 1.9 and one $C_{8-18}$-alkylbenzylsulfonate.

The weight ratio of surfactant to alkoxylate is generally in the range of from 1:99 to 70:30, preferably in the range of from 5:95 to 50:50, especially preferably in the range of from 25:75 to 40:60.

In most cases, the composition comprises from 1 to 80% by weight (preferably from 3 to 50, especially preferably from 5 to 30 and in particular from 8 to 20% by weight) of the total of surfactant and alkoxylate.

The compositions according to the invention can furthermore also comprise adjuvants conventionally used for agrochemical formulations, the choice of the adjuvants depending on the specific use form, the type of formulation or the active substance. Examples of suitable adjuvants are solvents, solid carriers, surface-active substances (such as surfactants, solubilizers, protective colloids, wetters and tackifiers), organic and inorganic thickeners, bactericides, antifreeze agents, antifoams, optionally colorants and adhesives (for example for the treatment of seed) or conventional adjuvants for bait formulations (for example attractants, feedants, bittering substances).

Suitable solvents are water or organic solvents such as mineral oil fractions of medium to high boiling point such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters, and strongly polar solvents, for example amines such as N-methylpyrrolidone. In principle, it is also possible to use solvent mixtures and mixtures of the abovementioned solvents and water.

Solid carriers are mineral earths such as silicas, silica gels, silicates, talc, kaolin, limestone, lime, chalk, bole, loess, clay, dolomite, diatomaceous earth, calcium and magnesium sulfate, magnesium oxide, ground synthetic materials, fertilizers such as ammonium sulfate, ammonium phosphate, ammonium nitrate, ureas and vegetable products such as cereal meal, tree bark meal, wood meal and nutshell meal, cellulose powders or other solid carriers.

Suitable thickeners are compounds which impart to the formulation a modified flow behavior, i.e. high viscosity at rest and low viscosity in the agitated state. Examples are polysaccharides, proteins (such as casein or gelatins), synthetic polymers, or inorganic layered minerals. Such thickeners are commercially available, for example Xanthan Gum (Kelzan®, CP Kelco, USA), Rhodopol® 23 (Rhodia, France) or Veegum® (R.T. Vanderbilt, USA) or Attaclay® (Engelhard Corp., NJ, USA). The thickener content in the formulation depends on the efficacy of the thickener. The skilled worker will choose such a content that the desired viscosity of the formulation is obtained. The content will amount to from 0.01 to 10% by weight in most cases.

Bactericides may be added in order to stabilize the composition. Examples of bactericides are those based on dichlorophene and benzyl alcohol hemiformal and also isothiazolinone derivatives such as alkylisothiazolinones and benzoisothiazolinones (Acticide® MBS from Thor Chemie). Examples of suitable antifreeze agents are ethylene glycol, propylene glycol, urea and glycerol. Examples of antifoams are silicone emulsions (such as, for example, Silikon® SRE, Wacker, Germany or Rhodorsil®, Rhodia, France), long-chain alcohols, fatty acids, salts of fatty acids, organofluorine compounds and mixtures of these.

The composition according to the invention can preferably be present in the form of an agrochemical formulation, water-soluble concentrates being preferred. Examples of formulations and their preparation are:

i) Water-soluble concentrates (SL, LS): 10 parts by weight of the active substances are dissolved using 90 parts by weight of water or a water-soluble solvent. Alternatively, wetters or other adjuvants are added. Upon dilution in water, the active substance dissolves. This gives a composition with an active substance content of 10% by weight.

ii) Dispersible concentrates (DC): 20 parts by weight of the active substances are dissolved in 70 parts by weight of cyclohexanone with addition of 10 parts by weight of a dispersant, for example polyvinylpyrrolidone. Upon dilution in water, a dispersion is obtained. The active substance content amounts to 20% by weight iii) Emulsifiable concentrates (EC): 15 parts by weight of the active substances are dissolved in 75 parts by weight of xylene with addition of calcium dodecylbenzene-sulfonate and castor oil ethoxylate (in each case 5 parts by weight). Upon dilution in water, an emulsion is obtained. The composition has an active substance content of 15% by weight.

iv) Emulsions (EW, EO, ES): 25 parts by weight of the active substances are dissolved in 35 parts by weight of xylene with addition of calcium dodecylbenzene-sulfonate and castor oil ethoxylate (in each case 5 parts by weight). Using an emulsifier (for example Ultra-Turrax), this mixture is placed into 30 parts by weight of water and made into a homogeneous emulsion. Upon dilution in water, an emulsion results. The composition has an active substance content of 25% by weight.

v) Suspensions (SC, OD, FS): 20 parts by weight of the active substances are comminuted with addition of 10 parts by weight of dispersants and wetters and 70 parts by weight of water or an organic solvent in a stirred-ball mill to give a finely divided active substance suspension. Upon dilution in water, a stable suspension of the active substance is obtained. The active substance content in the composition amounts to 20% by weight.

vi) Water-dispersible and water-soluble granules (WG, SG): 50 parts by weight of the active substances are ground finely with addition of 50 parts by weight of dispersants and wetters and formulated as water-dispersible or water-soluble granules by means of technical apparatuses (for example extrusion, spray tower, fluidized bed). Upon dilution in water, a stable dispersion or solution of the active substance is obtained. The composition has an active substance content of 50% by weight.

vii) Water-dispersible and water-soluble powders (WP, SP, SS, WS): 75 parts by weight of the active substances are ground in a rotor-stator mill with addition of 25 parts by weight of dispersants and wetters and also silica gel. Upon dilution in water, a stable dispersion or solution of the active substance is obtained. The active substance content of the composition amounts to 75% by weight.

viii) Gels (GF): in a ball mill, 20 parts by weight of the active substances, 10 parts by weight of dispersant, 1 part by weight of gelling agent and 70 parts by weight of water or an organic solvent are ground to give a fine suspension. Upon dilution with water, a stable suspension with an active substance content of 20% by weight is obtained.

ix) Dusts (DP, DS): 5 parts by weight of the active substances are ground finely and mixed intimately with 95 parts by weight of finely divided kaolin. This gives a dust with an active substance content of 5% by weight.

x) Granules (GR, FG, GG, MG): 0.5 part by weight of the active substances is ground finely and associated with 99.5 parts by weight of carriers. Conventional methods to this end are extrusion, spray-drying or the fluidized bed. This gives granules for direct application with an active substance content of 0.5% by weight.

xi) ULV solutions (UL): 10 parts by weight of the active substances are dissolved in 90 parts by weight of an organic solvent, for example xylene. This gives a composition to be applied directly with an active substance content of 10% by weight.

In general, the compositions comprise from 0.01 to 95% by weight, preferably from 0.1 to 90% by weight, of the pesticides.

The user will generally use the composition according to the invention for use in a premetering device, in a knapsack sprayer, in a spray tank or in a spraying aircraft. Here, the formulation is brought to the desired use concentration with a liquid, usually water and/or buffer, optionally with addition of further auxiliaries, whereby the ready-to-use spray mixture (known as a tank mix) is obtained. Usually, 50 to 500 liters of the ready-to-use spray mixture are applied per hectare of utilizable agricultural area, preferably from 100 to 400 liters. In specific segments the amounts may also be above (e.g., fruit growing) or below (e.g., aircraft application) these amounts. In specific cases, such as, for example, aircraft application, it is also possible to use an organic solvent for making up the spray mixture, instead of water.

The active substance concentrations in the ready-to-use preparations may be varied within substantial ranges. In general, they are between 0.0001 and 10%, preferably between 0.01 and 1%.

The concentration of the total of surfactant and alkoxylate in the ready-to-use preparation is in most cases in the range of from 0.01 to 50 g/l, preferably 0.08 to 10 g/l and in particular 0.5 to 8 g/l.

Oils of various types, wetters, drift reduction agents, stickers, spreaders, adjuvants, fertilizers, plant-strengthening products, trace elements, herbicides, bactericides, fungicides and/or pesticides may be added to the active substances or to the preparations comprising them, optionally also to the tank mix, immediately prior to use. These products can be admixed to the compositions according to the invention in the weight ratio 1:100 to 100:1, preferably 1:10 to 10:1. Depending on the nature of the desired effect, the application rates of the active substance when used in plant protection are between 0.001 and 2.0 kg of active substance per ha, preferably between 0.005 and 2 kg per ha, especially preferably between 0.05 and 0.9 kg per ha, in particular between 0.1 and 0.75 kg per ha.

The application rate of the total of surfactant and alkoxylate is in most cases in the range of from 10 to 3000 g/ha, preferably from 10 to 1000 g/ha, especially preferably from 80 to 750 g/ha and specifically from 200 to 400 g/ha.

The present invention furthermore relates to a concentrate comprising the surfactant and the amine alkoxylate (A) or the quaternized derivative (AQ) of the amine alkoxylate (A). This concentrate is particularly suitable for use as an additive to the tank mix. Suitable and preferred embodiments of the surfactant, the amine alkoxylate (A) and the quaternized derivative (AQ) of the amine alkoxylate (A) are as mentioned above. The weight ratio of surfactant to alkoxylate is usually in the range of from 1:99 to 70:30, preferably in the range of from 5:95 to 50:50, especially preferably in the range of from 25:75 to 40:60. The concentrate may optionally comprise solvents such as water or organic solvents. The concentrate may optionally comprise adjuvants such as the abovementioned adjuvants.

The present invention furthermore relates to a method for the preparation of the composition according to the invention by
 a) bringing the concentrate according to the invention and a pesticide into contact; or
 b) by bringing the pesticide, the surfactant and the amine alkoxylate (A) or the quaternized derivative (AQ) of the amine alkoxylate (A) into contact.

In a preferred embodiment, the method is a method of preparing a tank mix comprising the composition, by bringing the surfactant into contact with a mixture comprising the pesticide and the amine alkoxylate. In most cases, the mixture is an aqueous mixture (such as a tank mix) which may comprise customary formulation auxiliaries. Here, the surfactant may be added in pure form or else in the form of a dilution in water or organic solvents. Further customary formulation auxiliaries can likewise be added, in addition to the surfactant. Further pesticides may also be added to the tank mix, such as at least one herbicide (for example glyphosate) and/or at least one insecticide and/or one fungicide (for example pyraclostrobin).

The present invention furthermore relates to a use of a surfactant for addition to a mixture (such as a tank mix) comprising the pesticide and the amine alkoxylate. The surfactant is preferably added in order to increase the biological activity of the pesticide.

The present invention furthermore relates to a method of controlling phytopathogenic fungi and/or undesired vegetation and/or undesired insect or mite attack and/or for regulating the growth of plants, wherein the composition according to the invention is allowed to act on the respective pests, their environment or the plants to be protected from the respective pest, on the soil and/or on undesirable plants and/or the crop plants and/or their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

Examples which may be mentioned are plants which, as the result of plant-breeding and recombinant measures, have acquired a tolerance for certain classes of herbicides, such as hydroxyphenylpyruvate dioxygenase (HPPD) inhibitors, acetolactate synthase (ALS) inhibitors such as, for example, sulfonylureas (EP-A 257 993, U.S. Pat. No. 5,013,659) or imidazolinones (for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors such as, for example, glyphosate (see, for example, WO 92/00377), glutamine synthetase (GS) inhibitors such as, for example, glufosinate (see, for example, EP-A 242 236, EP-A 242 246) or oxynil herbicides (see, for example, U.S. Pat. No. 5,559,024). For example, breeding and mutagenesis have given rise to Clearfield® oilseed rape (BASF SE, Germany), which features tolerance for imidazolinones, for example imazamox. With the aid of recombinant methods, crop plants such as soybeans, cotton, maize, beet and oilseed rape have been generated which are resistant to glyphosate or glufosinate, and these are available by the brand names RoundupReady® (glyphosate-resistant, Monsanto, U.S.A.) and Liberty Link® (glufosinate-resistant, Bayer CropScience, Germany).

Also comprised are plants which, with the aid of recombinant measures, produce one or more toxins, for example those from the bacterial strain *Bacillus*. Toxins which are produced by such genetically modified plants comprise, for example, insecticidal proteins of *Bacillus* spp., in particular from *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetable insecticidal proteins (VIPs), for example VIP1, VIP2, VIP3, or VIP3A; insecticidal proteins from nematode-colonizing bacteria, for example *Photorhabdus* spp. or *Xenorhabdus* spp.; toxins from animal organisms, for example wasp, spider or scorpion toxins; fungal toxins, for example from Streptomycetes; plant lectins, for example from pea or barley; agglutinins; proteinase inhibitors, for example trypsin inhibitors, serine protease inhibitors, patatin, cystatin or papain inhibitors; ribosome-inactivating proteins (RIPs), for example ricin, maize RIP, abrin, luffin, saporin or bryodin; steroid-metabolizing enzymes, for example 3-hydroxysteroid oxidase, ecdysteroid IDP glycosyl transferase, cholesterol oxidase, ecdysone inhibitors or HMG CoA-reductase; ion channel blockers, for example inhibitors of sodium or calcium channels; juvenile hormone esterase; receptors for the diuretic hormone (helicokinin receptors); stilbene synthase, bibenzyl synthase, chitinases and glucanases. These toxins can also be produced, in the plants, in the form of pretoxins, hybrid proteins, truncated or otherwise modified proteins. Hybrid proteins are distinguished by a novel combination of different protein domains (see, for example, WO 2002/015701). Further examples of such toxins or genetically modified plants which produce these toxins are disclosed in EP-A 374 753, WO 93/07278, WO 95/34656, EP-A 427 529, EP-A 451 878, WO 03/18810 and WO 03/52073. The methods for generating these genetically modified plants are known to the skilled worker and explained, for example, in the abovementioned publications. A large number of the abovementioned toxins impart to the plants which produce them a tolerance for pests from all taxonomic classes of the arthropods, in particular beetles (Coeleropta), dipterans (Diptera) and lepidopterans (Lepidoptera) and nematodes (Nematoda). Genetically modified plants which produce one or more genes which code for insecticidal toxins are described for example in the abovementioned publications and are in some cases commercially available such as, for example, YieldGard® (maize varieties which produce the toxin Cry1Ab), YieldGard® Plus (maize varieties which produce the toxins Cry1Ab and Cry3Bb1), Starlink® (maize varieties which produce the toxin Cry9c), Herculex® RW (maize varieties which produce the toxins Cry34Ab1, Cry35Ab1 and the enzyme phosphinothricin N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIP-COT® (cotton varieties which produce a VIP toxin); NewLeaf® (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France, (maize varieties which produce the toxin Cry1Ab and the PAT enzyme), MIR604 from Syngenta Seeds SAS, France (maize varieties which produce a modified version of the toxin Cry3A, see in this context WO 03/018810), MON 863 from Monsanto Europe S.A., Belgium (maize varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (maize varieties which produce the toxin Cry1F and the PAT enzyme).

Also comprised are plants which, with the aid of recombinant measures, produce one or more proteins which bring about an increased resistance to, or ability to withstand, bacterial, viral or fungal pathogens such as, for example, so-called pathogenesis-related proteins (PR proteins, see EP-A 0 392 225), resistance proteins (for example potato varieties which produce two resistance genes against *Phytophthora infestans* from the Mexican wild potato *Solanum bulbocastanum*) or T4 lysozyme (for example potato varieties which, as the result of the production of this protein, are resistant to bacteria such as *Erwinia amylvora*).

Also comprised are plants whose productivity has been improved with the aid of recombinant methods, for example by increasing the yield potential (for example biomass, grain yield, starch content, oil content or protein content), the tolerance for drought, salt or other limiting environmental factors, or the resistance to pests and fungal, bacterial and viral pathogens.

Also comprised are plants whose constituents, in particular for improving human or animal nutrition, have been modified with the aid of recombinant methods, for example by oil plants producing health-promoting long-chain omega-3-fatty acids or monounsaturated omega-9-fatty acids (for example Nexera® oilseed rape, DOW Agro Sciences, Canada).

The present invention also relates to seed (such as seeds or other plant propagation materials) comprising the composition according to the invention. Plant propagation materials can be treated preventively with the composition according to the invention at the point of or even before sowing or at the point of or even before transplanting. For the treatment of seed, one will generally use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted form or, preferably, in diluted form. Here, the composition in question can be diluted 2- to 10-fold, so that from 0.01 to 60% by weight, preferably from 0.1 to 40% by weight, of active substance is present in the compositions used for the seed dressing. The application may be effected before or during sowing. The treatment of plant propagation material, in particular the treatment of seed, is known to the skilled worker and carried out by dusting, coating, pelleting, dipping or soaking the plant propagation material, the treatment preferably being carried out by pelleting, coating and dusting or by in-furrow treatment so that, for example, untimely early germination of the seed is prevented. It is preferred to use suspensions for the treatment of seed. Usually, such compositions comprise from 1 to 800 g/l of active substance, from 1 to 200 g/l of surfactants, from 0 to 200 g/l of antifreeze agents, from 0 to 400 g/l of binders, from 0 to 200 g/l of colorants and solvent, preferably water.

The advantages of the invention are high stability of the formulation and of the spray mixture, little wind-caused drift in the case of spray applications, good adhesion of the formulation on the surface of the treated plants, increased solubility of the pesticides in the formulation, increased permeation of the pesticides into the plant and, as a result, more rapid and enhanced activity. An important advantage is the low toxicity of the alkoxylates, in particular the low aquatic toxicity. Another advantage is the low harmful effect against crop plants, i.e., low phytotoxic effects. A further advantage is the simple handling of these alkoxides since, for example, no gelling takes place upon their incorporation into formulations. Another advantage is that no phase separation and no salt precipitation occurs in compositions with a high salt content, such as over 400 g/l glyphosate; but the alkoxylates are highly compatible with surfactants, specifically anionic surfactants.

Another important advantage is that the invention permits the stable formulation of anionic, H-acidic pesticides in the presence of cationic surfactants. This was particularly surprising since usually the precipitation of salts may occur in compositions which comprise anionic and cationic compounds, for example during storage, in the spray mixture or in another dilution.

The examples which follow illustrate the invention without imposing any limitation.

EXAMPLES

Surfactant A: $C_{10-13}$-alkylbenzenesulfonate, free acid.
Surfactant B: Phosphate ester of $C_{10-12}$-alkanol alkoxylate, the alkoxylate being composed of ethylene oxide and/or propylene oxide, and having a mean number of alkoxide units in the range of from 12 to 18.
Surfactant C: $C_{16-18}$-alkanol alkoxylate, the alkoxylate being composed of ethylene oxide and propylene oxide, and having a mean number of alkoxide units in the range of from 17 to 26.
Surfactant D: iso-$C_{13}$-alkanol alkoxylate, the alkoxylate being composed of ethylene oxide and having a mean number of alkoxide units in the range of from 4.5 to 8.
Surfactant E: $C_{10}$-guerbet alkanol alkoxylate, the alkoxylate being composed of ethylene oxide and having a mean number of alkoxide units in the range of from 2.5 to 6.
Surfactant F: $C_{4-8}$-alkanol alkoxylate, the alkoxylate being composed of ethylene oxide and having a mean number of alkoxide units in the range of from 3.5 to 7.
Surfactant G: Fatty acid mixture comprising 50-60% dodecanoic acid and 20-30% of $C_{14}$-alkanolic acid, and further $C_{10-18}$-alkanoic acids, acid number 250-260.
Surfactant H: $C_{8-10}$-alkylpolyglucoside, D.P. 1.7.

Example 1

Preparation of Amine Alkoxylate A

First, 2-propylheptylamine was prepared starting from 2-propylheptanol and ammonia, as described in Example 1 of PCT/EP2011/050369.

Then 1280 g (8.15 mol) of the 2-propylheptylamine were admixed with 40 g of water. Then, after flushing with nitrogen, at 100° C., 717 g (16.3 mol) of ethylene oxide were metered in (2 bar, 16 h). Subsequently, at 90° C., remaining traces of ethylene oxide were removed under reduced pressure. This gave a quantitative yield with an amine number of 229 mg KOH/g. In the next step, 821.5 g (3.35 mol) of this precursor product were admixed with 8.0 g of 50% strength KOH and dewatering was carried out at 90° C. under reduced pressure. After flushing with nitrogen, at 120° C., 1179 g (=26.8 mol) of ethylene oxide were metered in (1.5 bar, 12 h). This gave a quantitative yield of the yellowish low-viscosity, liquid amine-alkoxylate A.

Example 2

Amine Alkoxylate+Surfactant A

For the greenhouse tests, winter wheat (cultivar Cubus) and soybean (cultivar Oxford) were sown or potted in loamy sandy soil to a depth of 1-2 cm. When the plants had reached a growth height of 10 to 25 cm (i.e., around 10 to 21 days after sowing), the spray mixtures were applied to the plants in a spraying cabin.

A concentrated formulation comprising glyphosate isopropylammonium in solution in water comprising the surfactants stated and amine alkoxylate A from Example 1 was diluted with deionized water and applied at a water application rate of 375 l/ha (140 g or 280 g of glyphosate/ha). The temperatures in the experimental period were between 18-35° C. During this time, the experimental plants received optimum watering, with nutrients being supplied via the water used for watering.

The herbicidal activity was evaluated by awarding scores to the treated plants (four each time) in comparison to the untreated control plants. The evaluation scale ranges from 0% to 100% activity. 100% activity means the complete death at least of those parts of the plant that are above ground. Conversely, 0% activity means that there were no differences between treated and untreated plants.

The results in Tables 1 demonstrate the increased activity of the active substance as a result of addition of the amine alkoxylate in admixture with surfactant.

TABLE 1A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Without [a] | — | 53 | 10 |
| Amine alkoxylate A [a] | 300 | 85 | 62 |
| Surfactant A [a] | 300 | 84 | 64 |
| Amine alkoxylate A + surfactant A | 255 + 45 | 86 | 85 |

[a] not according to the invention

TABLE 1B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Without [a] | — | 68 | 10 |
| Amine alkoxylate A [a] | 300 | 86 | 78 |
| Surfactant A [a] | 300 | 90 | 71 |
| Amine alkoxylate A + surfactant A | 255 + 45 | 93 | 88 |

[a] not according to the invention

TABLE 1C

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 75 | 54 |
| Amine alkoxylate A + surfactant A | 350 + 50 | 86 | 73 |

[a] not according to the invention

TABLE 1D

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 83 | 69 |
| Amine alkoxylate A + surfactant A | 350 + 50 | 94 | 94 |

[a] not according to the invention

Example 3

Amine Alkoxylate+Surfactant A+Surfactant B

The experiments were carried out as in Example 2 and the results are compiled in Table 2.

TABLE 2A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 75 | 54 |
| Surfactant B [a] | 100 | 63 | 39 |
| Amine alkoxylate A + surfactant A + surfactant B | 250 + 50 + 100 | 81 | 61 |

[a] not according to the invention

TABLE 2B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 83 | 69 |
| Surfactant B [a] | 100 | 73 | 50 |
| Amine alkoxylate A + surfactant A + surfactant B | 250 + 50 + 100 | 95 | 83 |

[a] not according to the invention

Example 4

Amine Alkoxylate+Surfactant A+Surfactant C

The experiments were carried out as in Example 2 and the results are compiled in Table 3.

TABLE 3A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 75 | 54 |
| Surfactant C [a] | 100 | 61 | 36 |
| Amine alkoxylate A + surfactant A + surfactant C | 250 + 50 + 100 | 90 | 78 |

[a] not according to the invention

TABLE 3B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 83 | 69 |
| Surfactant C [a] | 100 | 68 | 39 |
| Amine alkoxylate A + surfactant A + surfactant C | 250 + 50 + 100 | 93 | 84 |

[a] not according to the invention

Example 5

Amine Alkoxylate+Surfactant A+Surfactant D

The experiments were carried out as in Example 2 and the results are compiled in Table 4.

TABLE 4A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 300 | 85 | 62 |
| Surfactant D [a] | 300 | 80 | 51 |
| Amine alkoxylate A + surfactant A + surfactant D | 200 + 50 + 50 | 88 | 75 |

[a] not according to the invention

TABLE 4B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 300 | 86 | 78 |
| Surfactant D [a] | 300 | 85 | 63 |
| Amine alkoxylate A + surfactant A + surfactant D | 200 + 50 + 50 | 91 | 85 |

[a] not according to the invention

Example 6

Amine Alkoxylate+Surfactant A+Surfactant E

The experiments were carried out as in Example 2 and the results are compiled in Table 5.

TABLE 5A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 300 | 85 | 62 |
| Surfactant E [a] | 300 | 78 | 53 |
| Amine alkoxylate A + surfactant A + surfactant E | 200 + 50 + 50 | 89 | 81 |

[a] not according to the invention

TABLE 5B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 300 | 86 | 78 |
| Surfactant E [a] | 300 | 81 | 76 |
| Amine alkoxylate A + surfactant A + surfactant E | 200 + 50 + 50 | 90 | 83 |

[a] not according to the invention

Example 7

Amine Alkoxylate+Surfactant E+Surfactant F

The experiments were carried out as in Example 2 and the results are compiled in Table 6.

TABLE 6A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 300 | 85 | 62 |
| Surfactant E [a] | 300 | 78 | 53 |
| Surfactant F [a] | 300 | 72 | 59 |
| Amine alkoxylate A + surfactant E + surfactant F | 200 + 50 + 50 | 85 | 80 |

[a] not according to the invention

TABLE 6B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 300 | 86 | 78 |
| Surfactant E [a] | 300 | 81 | 76 |
| Surfactant F [a] | 300 | 81 | 80 |
| Amine alkoxylate A + surfactant E + surfactant F | 200 + 50 + 50 | 89 | 92 |

[a] not according to the invention

Example 8

Amine Alkoxylate+Surfactant A+Surfactant G

The experiments were carried out as in Example 2 and the results are compiled in Table 7.

TABLE 7A

Efficacy after 21 days at 140 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 75 | 54 |
| Amine alkoxylate A + surfactant A + surfactant G | 250 + 50 + 100 | 83 | 65 |

[a] not according to the invention

TABLE 7B

Efficacy after 21 days at 280 g/ha glyphosate

| Amine alkoxylate/surfactant | Amount [g/ha] | Winter wheat efficacy [%] | Soybean efficacy [%] |
|---|---|---|---|
| Amine alkoxylate A [a] | 400 | 83 | 69 |
| Amine alkoxylate A + surfactant A + surfactant G | 250 + 50 + 100 | 90 | 85 |

[a] not according to the invention

Example 9

Stability Test

An aqueous solution composed of 480 g/l glyphosate isopropylamine salt, 225 g/l amine alkoxylate A and 75 g/l surfactant H was stored for four weeks, either at −5° C. or +55° C. No phase separation occurred.

By way of comparison, an aqueous solution composed of 480 g/l of glyphosate isopropylamine salt and 300 g/l of Genamine® T 150 ($C_{16/18}$-amine ethoxylate having 15 EO units, commercially available from Clariant) was stored correspondingly. A clear phase separation into an aqueous bottom phase with glyphosate salt and a top phase with Genamine® T150 occurred.

By way of further comparison, an aqueous solution composed of 480 g/l of glyphosate isopropylamine salt, 150 g/l of Genamine® T 150 and 150 g/l surfactant H was stored correspondingly. Likewise, a clear phase separation into an aqueous bottom phase with glyphosate salt and a top phase with Genamine® T150 occurred.

We claim:

1. A composition comprising a pesticide, a surfactant and an alkoxylate, wherein the alkoxylate is an amine alkoxylate (A)

$$R^7-N\begin{Bmatrix}[R^1-O]_n-R^6\\[R^2-O]_m-R^6\end{Bmatrix} \quad (A)$$

or a quaternized derivative (AQ)

$$R^7-\overset{R^3}{\underset{+}{N}}\begin{Bmatrix}[R^1-O]_n-R^6\\[R^2-O]_m-R^6\end{Bmatrix} A^- \quad (AQ)$$

of the amine alkoxylate (A), where
$-(R^1O)_n-$, $-(R^2O)_m-$, and $-(R^5O)_p-$ and independently of one another are alkoxylate chains comprising ethylene oxide, propylene oxide, butylene oxide or a mixture thereof,
$R^3$ is an H, —OH, —OR$^4$, —[R$^5$—O]$_p$—R$^6$, $C_1$-$C_6$-alkyl or an oxygen anion,
$R^4$ is a $C_1$-$C_6$-alkyl, $C_2$-$C_6$-alkenyl or $C_2$-$C_6$-alkynyl,
$R^6$ is an H, $C_1$-$C_6$-alkyl, $C_2$-$C_6$-alkenyl, $C_2$-$C_6$-alkynyl, —SO$_3$R$^a$, —P(O)OR$^b$OR$^c$, —CH$_2$CO$_2$R$^d$, or —C(O)R$^e$,
$R^7$ is 2-propylheptyl, $R^a$ and $R^d$ independently of one another are an H, inorganic or organic cations, $R^b$ and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_2$-$C_{22}$-alkenyl, $C_2$-$C_{22}$-alkynyl, $C_6$-$C_{22}$-aryl or $C_7$-$C_{22}$-alkylaryl, n, m and p independently of one another have a value of from 1 to 30, $A^-$ is an agriculturally acceptable anion, or, if $R^3$ is an oxygen anion, $A^-$ is absent;

and wherein at least one surfactant is selected from the group of surfactants consisting of
a) a $C_{6-18}$-alkylpolyglucoside, with a degree of polymerization of from 1.2 to 1.9, and
b) a $C_{8-18}$-alkylbenzenesulfonate.

2. The composition according to claim 1, wherein the weight ratio of surfactant to alkoxylate is in the range of from 1:99 to 70:30.

3. The composition according to claim 1, wherein the composition comprises from 1 to 80% by weight of the total of surfactant and alkoxylate.

4. The composition according to claim 1, wherein the composition comprises at least two different surfactants.

5. A composition comprising a pesticide, a surfactant and an alkoxylate, wherein the alkoxylate is an amine alkoxylate (A)

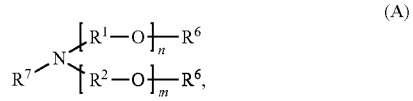

(A)

or a quaternized derivative (AQ)

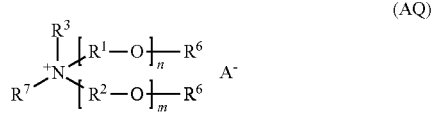

(AQ)

of the amine alkoxylate (A), where
$-(R^1O)_n-$, $-(R^2O)_m-$, and $-(R^5O)_p-$ and independently of one another are alkoxylate chains comprising ethylene oxide, propylene oxide, butylene oxide or a mixture thereof, $R^3$ is an H, —OH, —OR$^4$, —[R$^5$—O]$_p$—R$^6$, $C_1$-$C_6$-alkyl or an oxygen anion, $R^4$ is a $C_1$-$C_6$-alkyl, $C_2$-$C_6$-alkenyl or $C_2$-$C_6$-alkynyl, $R^6$ is an H, $C_1$-$C_6$-alkyl, $C_2$-$C_6$-alkenyl, $C_2$-$C_6$-alkynyl, —SO$_3$R$^a$, —P(O)OR$^b$OR$^c$, —CH$_2$CO$_2$R$^d$, or —C(O)R$^e$, $R^7$ is 2-propylheptyl, $R^a$ and $R^d$ independently of one another are an H, inorganic or organic cations, $R^b$ and $R^c$ independently of one another are an H, inorganic or organic cations, $C_1$-$C_6$-alkyl, $C_2$-$C_6$-alkenyl or $C_2$-$C_6$-alkynyl, $R^e$ is $C_1$-$C_{22}$-alkyl, $C_2$-$C_{22}$-alkenyl, $C_2$-$C_{22}$-alkynyl, $C_6$-$C_{22}$-aryl or $C_7$-$C_{22}$-alkylaryl, n, m and p independently of one another have a value of from 1 to 30, $A^-$ is an agriculturally acceptable anion, or, if $R^3$ is an oxygen anion, $A^-$ is absent;

wherein the surfactant is selected from the group consisting of:
a) a $C_{16-18}$-alkanol alkoxylate, where the alkoxylate is composed of ethylene oxide and/or propylene oxide, and the alkanol alkoxylate has a mean number of alkoxide units in the range of from 12 to 35;
b) a $C_{10}$-guerbet alkanol alkoxylate, where the alkoxylate is composed of ethylene oxide and the alkanol alkoxylate has a mean number of alkoxide units in the range of from 2 to 8;
c) an iso-$C_{13}$-alkanol alkoxylate, where the alkoxylate is composed of ethylene oxide and the alkanol alkoxylate has a mean number of alkoxide units in the range of from 3 to 10;
d) a $C_{4-8}$-alkanol alkoxylate, where the alkoxylate is composed of ethylene oxide and the alkanol alkoxylate has a mean number of alkoxide units in the range of from 2 to 9; and
g) a phosphate ester of $C_{8-14}$-alkanol alkoxylates.

6. The composition according to claim 1, wherein at least one surfactant is a $C_{8-10}$-alkylpolyglucoside with a degree of polymerization of from 1.4 to 1.9.

7. The composition according to claim 1, wherein $R^1$, $R^2$ and $R^5$ independently of one another are ethylene, ethylene and propylene, ethylene and butylene, or ethylene, propylene and butylene.

8. The composition according to claim 1, wherein the pesticide is a pesticide with at least one H-acidic group or an anionic salt of the pesticide with at least one H-acidic group.

9. The composition according to claim 1, wherein, in the amine alkoxylate (A), the total of n and m is from 2 to 40, and in its quaternized derivative (AQ) the total of n, m and p is from 3 to 80.

10. The composition according to claim 1, wherein $R^3$ is an H.

11. The composition according to claim 1, wherein the pesticide comprises a pesticide with at least one H-acidic group.

12. A concentrate comprising the composition according to claim 1.

13. A method of controlling phytopathogenic fungi and/or undesired vegetation and/or undesired insect or mite attack and/or for regulating the growth of plants, wherein the composition according to claim 1 is allowed to act on the respective pests, their environment or the plants to be protected from the respective pest, on the soil and/or on undesired plants and/or the crop plants and/or their environment.

14. The method according to claim 13, wherein the surfactant is an anionic surfactant comprising an anionic group, which is a sulfonate, sulfate, phosphate or carboxylate; and/or a nonionic surfactant, which is a sugar-based surfactant or an alkanol alkoxylate.

15. The method according to claim 13, wherein the weight ratio of surfactant to alkoxylate is in the range of from 1:99 to 70:30.

16. The method according to claim 13, wherein the composition comprises from 1 to 80% by weight of the total of surfactant and alkoxylate.

17. The method according to claim 13, wherein the composition comprises at least two different surfactants.

18. The method according to claim 13, wherein at least one surfactant is selected among the following surfactants:
a) a $C_{16-18}$-alkanol alkoxylate, where the alkoxylate is composed of ethylene oxide and/or propylene oxide, and the alkanol alkoxylate has a mean number of alkoxide units in the range of from 12 to 35;

b) a $C_{10}$-guerbet alkanol alkoxylate, where the alkoxylate is composed of ethylene oxide and the alkanol alkoxylate has a mean number of alkoxide units in the range of from 2 to 8;

c) an iso-$C_{13}$-alkanol alkoxylate, where the alkoxylate is composed of ethylene oxide and the alkanol alkoxylate has a mean number of alkoxide units in the range of from 3 to 10;

d) a $C_{4-8}$-alkanol alkoxylate, where the alkoxylate is composed of ethylene oxide and the alkanol alkoxylate has a mean number of alkoxide units in the range of from 2 to 9;

e) a $C_{8-10}$-alkylpolyglucoside, with a degree of polymerization of from 1.4 to 1.9;

f) a $C_{8-14}$-alkylbenzenesulfonate; and g) a phosphate ester of $C_{8-14}$-alkanol alkoxylates.

19. Seed treated with the composition according to claim 1.

20. The composition according to claim 1, wherein the pesticide is a pesticide with at least one H-acidic group or an anionic salt of the pesticide with at least one H-acidic group, selected from the group consisting of glyphosate, glufosinate, imazamethabenz, imazamox, imazapic, imazapyr, imazaquin and imazethapyr.

21. The composition according to claim 1, wherein the $C_{8-18}$-alkylbenzenesulfonate is a $C_{10-13}$-alkylbenzenesulfonate.

* * * * *